United States Patent
Ryan et al.

(10) Patent No.: US 12,259,086 B2
(45) Date of Patent: Mar. 25, 2025

(54) ADJUSTABLE IMAGE CAPTURE DEVICE

(71) Applicant: Becton, Dickinson and Company, Franklin Lakes, NJ (US)

(72) Inventors: Kevin M. Ryan, Whitehouse Station, NJ (US); Sagar S Deyagond, Vijayapura (IN); Ashley Rachel Rothenberg, Morris Plains, NJ (US); Jessica Su, Bayside, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 181 days.

(21) Appl. No.: 17/993,486

(22) Filed: Nov. 23, 2022

(65) Prior Publication Data

US 2024/0167617 A1    May 23, 2024

(51) Int. Cl.
| | |
|---|---|
| *F16M 11/28* | (2006.01) |
| *A61G 7/05* | (2006.01) |
| *F16M 11/10* | (2006.01) |
| *F16M 11/18* | (2006.01) |
| *F16M 11/20* | (2006.01) |
| *G03B 17/56* | (2021.01) |
| *H04N 23/50* | (2023.01) |
| *H04N 23/695* | (2023.01) |

(52) U.S. Cl.
CPC ........... *F16M 11/28* (2013.01); *A61G 7/0524* (2016.11); *F16M 11/10* (2013.01); *F16M 11/18* (2013.01); *F16M 11/2014* (2013.01); *G03B 17/561* (2013.01); *H04N 23/555* (2023.01); *H04N 23/695* (2023.01); *F16M 2200/024* (2013.01)

(58) Field of Classification Search
None
See application file for complete search history.

(56) References Cited

U.S. PATENT DOCUMENTS

| | | | |
|---|---|---|---|
| 2008/0136915 A1 | 6/2008 | Iwamura | |
| 2012/0209070 A1* | 8/2012 | Piech | A61B 1/044 600/110 |
| 2014/0048672 A1* | 2/2014 | Woodruff | F16M 11/18 248/404 |
| 2015/0326764 A1 | 11/2015 | Roshanravan | |
| 2017/0034319 A1* | 2/2017 | Chenn | H04N 1/00103 |
| 2020/0180142 A1 | 6/2020 | Chow et al. | |

* cited by examiner

*Primary Examiner* — Rodney E Fuller
(74) *Attorney, Agent, or Firm* — The Webb Law Firm

(57) ABSTRACT

A adjustable image capture device that includes a housing, a linkage assembly having a bore and including a plurality of linkages, and where each linkage has a bore, and the bores of the plurality of linkages define the bore of the linkage assembly, and an image capture device, wherein the image capture device is configured to fit within a bore of the linkage assembly, where the linkage assembly is configured to fit within the housing, where, when the linkage assembly is in a first state, each linkage of the plurality of linkages are positioned inside a channel of the housing, and where, when the linkage assembly is in a second state, one or more of the linkages of the plurality of linkages are positioned outside the channel of the housing.

30 Claims, 16 Drawing Sheets

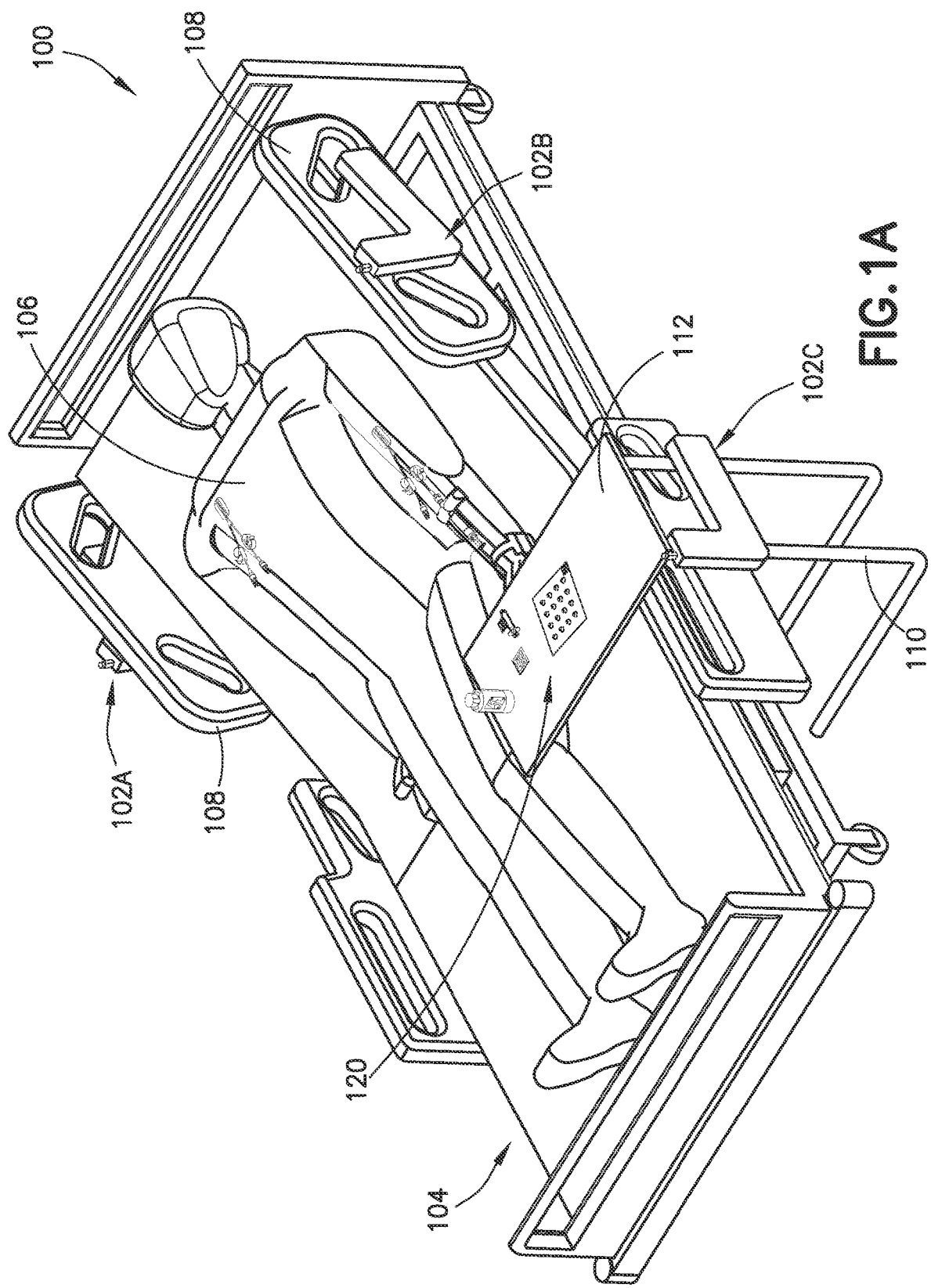

ADJUSTABLE IMAGE CAPTURE DEVICE

BACKGROUND

Computer vision may refer to a scientific field that deals with how computers may gain high-level understanding from images and/or videos. Computer vision may include theories behind how artificial systems may extract information from images and/or videos. The image data can take many forms, such as video sequences, views from multiple cameras, multi-dimensional data from a 3D scanner, or medical scanning devices. Computer vision techniques may include methods for acquiring, processing, analyzing and understanding images or videos, and extracting high-dimensional data from the real world in order to produce numerical or symbolic information, which may be in the form of decisions to be made. Computer vision systems may be used in different settings, such as in location were medical treatments are being applied.

However, obtaining images may require adequate camera vantage angles. This is particularly a challenge in situations where an object may be in a wide range of locations or orientations, in relation to any single fixed camera point, even if that camera has multiple degrees of freedom of movement (e.g., including pan and tilt movement). This challenge becomes even more difficult with regard to patient applications, particular in Hospitals, where the objects may need to be tracked, even when the objects are moved to various locations, at various orientation angles and with view blocking obstructions (e.g., a medical service provider such as, a clinician, is in between an object and a camera).

SUMMARY

Accordingly, aspects of the present disclosure is directed to non-limiting embodiments of an improved adjustable image capture device.

In accordance with an embodiment of the present invention, an adjustable image capture device includes a housing; a linkage assembly, the linkage assembly having a bore, the linkage assembly comprising a plurality of linkages, and wherein each linkage having a bore, wherein the bores of the plurality of linkages defining the bore of the linkage assembly; and an image capture device, wherein the image capture device is configured to fit within a bore of the linkage assembly; wherein the linkage assembly is configured to fit within the housing; wherein, when the linkage assembly is in a first state, each linkage of the plurality of linkages are positioned inside a channel of the housing; wherein, when the linkage assembly is in a second state, one or more of the linkages of the plurality of linkages are positioned outside the channel of the housing.

In accordance with an embodiment of the present invention, the adjustable image capture device includes a pan motor assembly, wherein the pan motor assembly comprises: a motor; and wherein the motor is attached to the image capture device, and wherein the motor is configured to impart motion to the image capture device.

In accordance with an embodiment of the present invention, each linkage of the plurality of linkages has a gear rack, wherein the adjustable image capture device further comprises: an extension motor assembly, wherein the extension motor assembly comprises: a gear; and a motor; wherein the gear has teeth that mesh with teeth of the gear rack, and wherein the motor is configured to impart motion to the gear; wherein the extension motor assembly is configured to extend the linkage assembly along a first axis.

In accordance with an embodiment of the present invention, the adjustable image capture device includes a tilt motor assembly, wherein the tilt motor assembly comprises: a motor; and wherein the motor is attached to the image capture device, and wherein the motor is configured to impart motion to the image capture device.

In accordance with an embodiment of the present invention, the housing has an opening that provides access the channel, and wherein the linkages of the linkage assembly are configured to fit through the opening.

In accordance with an embodiment of the present invention, the bore of a linkage is a primary bore, wherein the plurality of linkages comprises a first linkage and a second linkage; wherein the first linkage has one or more secondary bores and the second linkage has one or more secondary bores; wherein the one or more secondary bores of the first linkage are adjacent the primary bore of the first linkage, wherein the one or more secondary bores of the second linkage are adjacent the primary bore of the second linkage; wherein a line is positioned in the one or more secondary bores of the first linkage and is positioned in the one or more secondary bores of the second linkage, wherein the line couples the first linkage to the second linkage.

In accordance with an embodiment of the present invention, the image capture device is a borescope camera.

In accordance with an embodiment of the present invention, the plurality of linkages comprises a first linkage and a second linkage, wherein the first linkage has a first surface, wherein the first surface comprises at least one magnet; and wherein the second linkage has a second surface, wherein the second surface comprises a material that is attracted to the magnet positioned on the first surface of the first linkage.

In accordance with an embodiment of the present invention, the first linkage and the second linkage are configured such that when the second surface of the second linkage is held in contact with the first surface of the first linkage based on the at least one magnet being attracted to the material of the second surface, the first linkage and the second linkage are in an aligned state.

In accordance with an embodiment of the present invention, the first surface of the first linkage comprises at least one protrusion, and wherein the at least one protrusion comprises the at least one magnet.

In accordance with an embodiment of the present invention, the second surface of the second linkage comprises at least one recess, wherein the at least one recess is sized and configured to receive the at least one protrusion of the first surface; and wherein the at least one recess is configured such that when the at least one recess receives the at least one protrusion, the first linkage and the second linkage are in an aligned state.

In accordance with an embodiment of the present invention, the at least one magnet positioned on the first surface is at least one first magnet, wherein at least one recess of the second surface comprises at least one second magnet, wherein the at least one first magnet is configured to be attracted to the at least one second magnet.

In accordance with an embodiment of the present invention, the adjustable image capture device includes a pan motor assembly, wherein the pan motor assembly comprises: a motor; and wherein the motor is coupled to the image capture device, and wherein the motor is configured to impart motion to the image capture device.

In accordance with an embodiment of the present invention, the linkage assembly comprises a first end and a second end, wherein the first end of the linkage assembly is adjacent an opening of the housing when the linkage assembly is in the first state; and wherein the pan motor assembly is attached to the linkage assembly adjacent the first end of the linkage assembly.

In accordance with an embodiment of the present invention, each linkage of the plurality of linkages has a gear rack, the adjustable image capture device further comprising: an extension motor assembly, wherein the extension motor assembly comprises: a gear; and a motor; wherein the gear has teeth that mesh with teeth of the gear rack, and wherein the motor is configured to impart motion to the gear; wherein the extension motor assembly is configured to extend the linkage assembly along a first axis; wherein the pan motor assembly is attached to the linkage assembly such that the pan motor assembly extends with the linkage assembly when the linkage assembly extends along the first axis.

In accordance with an embodiment of the present invention, the housing comprises a cavity, wherein the pan motor assembly is sized and configured to fit within the cavity.

In accordance with an embodiment of the present invention, the pan motor assembly is positioned within the cavity when the linkage assembly is in the first state.

In accordance with an embodiment of the present invention, an adjustable image capture device includes a housing; a linkage assembly, the linkage assembly having a bore, the linkage assembly comprising a plurality of linkages, wherein each linkage of the plurality of linkages has a gear rack, and wherein each linkage having a bore, wherein the bores of the plurality of linkages defining the bore of the linkage assembly; and an extension motor assembly, wherein the extension motor assembly comprises: a gear, and a motor, and wherein the gear has teeth that mesh with teeth of the gear rack, wherein the motor is configured to impart motion to the gear, and wherein the extension motor assembly is configured to extend the linkage assembly along a longitudinal axis; and an image capture device, wherein the image capture device is configured to fit within the bore of the linkage assembly; wherein the linkage assembly is configured to fit within the housing; wherein, when the linkage assembly is in a first state, each linkage of the plurality of linkages are positioned inside a channel of the housing; wherein, when the linkage assembly is in a second state, one or more of the linkages of the plurality of linkages are positioned outside the channel of the housing; wherein extension motor assembly is configured to transition the linkage assembly from the first state to the second state.

In accordance with an embodiment of the present invention, the second state comprising a plurality of sub-states, wherein each sub-state of the plurality of sub-states defines a position of a linkage relative to the housing; and wherein each sub-state of the plurality of sub-states is associated with a position of the teeth of the gear relative to the teeth of the gear rack.

In accordance with an embodiment of the present invention, the adjustable image capture device including a tilt motor assembly, wherein the tilt motor assembly comprises: a motor; and wherein the motor is attached to the image capture device, and wherein the motor is configured to impart motion to the image capture device.

In accordance with an embodiment of the present invention, the image capture device comprises a borescope camera, wherein the borescope camera has a field of view, and wherein the borescope camera is configured such that the field of view is biased in a first direction.

In accordance with an embodiment of the present invention, when the tilt motor assembly is activated, the field of view is adjusted to a second direction and wherein there is angle between the first direction and the second direction.

In accordance with an embodiment of the present invention, the adjustable image capture device including a pan motor assembly, wherein the pan motor assembly comprises: a motor; and wherein the motor is attached to the image capture device, and wherein the motor is configured to impart motion to the image capture device.

In accordance with an embodiment of the present invention, the motor comprises a servo-motor.

In accordance with an embodiment of the present invention, an adjustable image capture device includes a housing; a linkage assembly, the linkage assembly having a bore, the linkage assembly comprising a plurality of linkages, wherein each linkage of the plurality of linkages has a gear rack, and wherein each linkage having a bore, wherein the bores of the plurality of linkages defining the bore of the linkage assembly; and an extension motor assembly, wherein the extension motor assembly comprises: a gear, and a first motor, and wherein the gear has teeth that mesh with teeth of the gear rack, and wherein the first motor is configured to impart motion to the gear, and wherein the extension motor assembly is configured to extend the linkage assembly along a first axis; a borescope camera, wherein the borescope camera is configured to fit within a bore of the linkage assembly; a pan motor assembly, wherein the pan motor assembly comprises a second motor, wherein the second motor is coupled to the borescope camera, wherein pan motor assembly is configured to rotate a field of view of the borescope camera about a second axis; and an tilt motor assembly, wherein the tilt motor assembly comprises a third motor, wherein the third motor is attached to the borescope camera, and wherein the tilt motor assembly is configured to rotate the field of view of the borescope camera about a third axis, wherein the second axis is perpendicular to the third axis; wherein the linkage assembly is configured to fit within the housing; wherein, when the linkage assembly is in a first state, each linkage of the plurality of linkages are positioned inside a channel of the housing; wherein, when the linkage assembly is in a second state, one or more of the linkages of the plurality of linkages are positioned outside the channel of the housing; wherein extension motor assembly is configured to transition the linkage assembly from the first state to the second state.

In accordance with an embodiment of the present invention, the borescope camera has a field of view and wherein the borescope camera is configured such that the field of view is biased such that the field of view is in a first direction.

In accordance with an embodiment of the present invention, when the tilt motor assembly is activated, the field of view is adjusted to a second direction and wherein there is angle between the first direction and the second direction.

In accordance with an embodiment of the present invention, the bore of a linkage is a primary bore, wherein the plurality of linkages comprises a first linkage and a second linkage; wherein the first linkage has one or more secondary bores and the second linkage has one or more secondary bores; wherein the one or more secondary bores of the first linkage are adjacent the primary bore of the first linkage, wherein the one or more secondary bores of the second linkage are adjacent the primary bore of the second linkage; wherein a line is positioned in the one or more secondary bores of the first linkage and is positioned in the one or more secondary bores of the second linkage, wherein the line couples the first linkage to the second linkage.

In accordance with an embodiment of the present invention, at least one of the first motor, the second motor, or the third motor comprises a servo-motor.

In accordance with an embodiment of the present invention, the housing has an opening that provides access the channel, and wherein the linkages of the linkage assembly are configured to fit through the opening.

BRIEF DESCRIPTION OF THE DRAWINGS

Additional advantages and details are explained in greater detail below with reference to the exemplary embodiments that are illustrated in the accompanying schematic figures, in which:

FIGS. 1A-1E are diagrams of a non-limiting embodiment of an implementation of an adjustable image capture device;

DETAILED DESCRIPTION

Figure 1B:
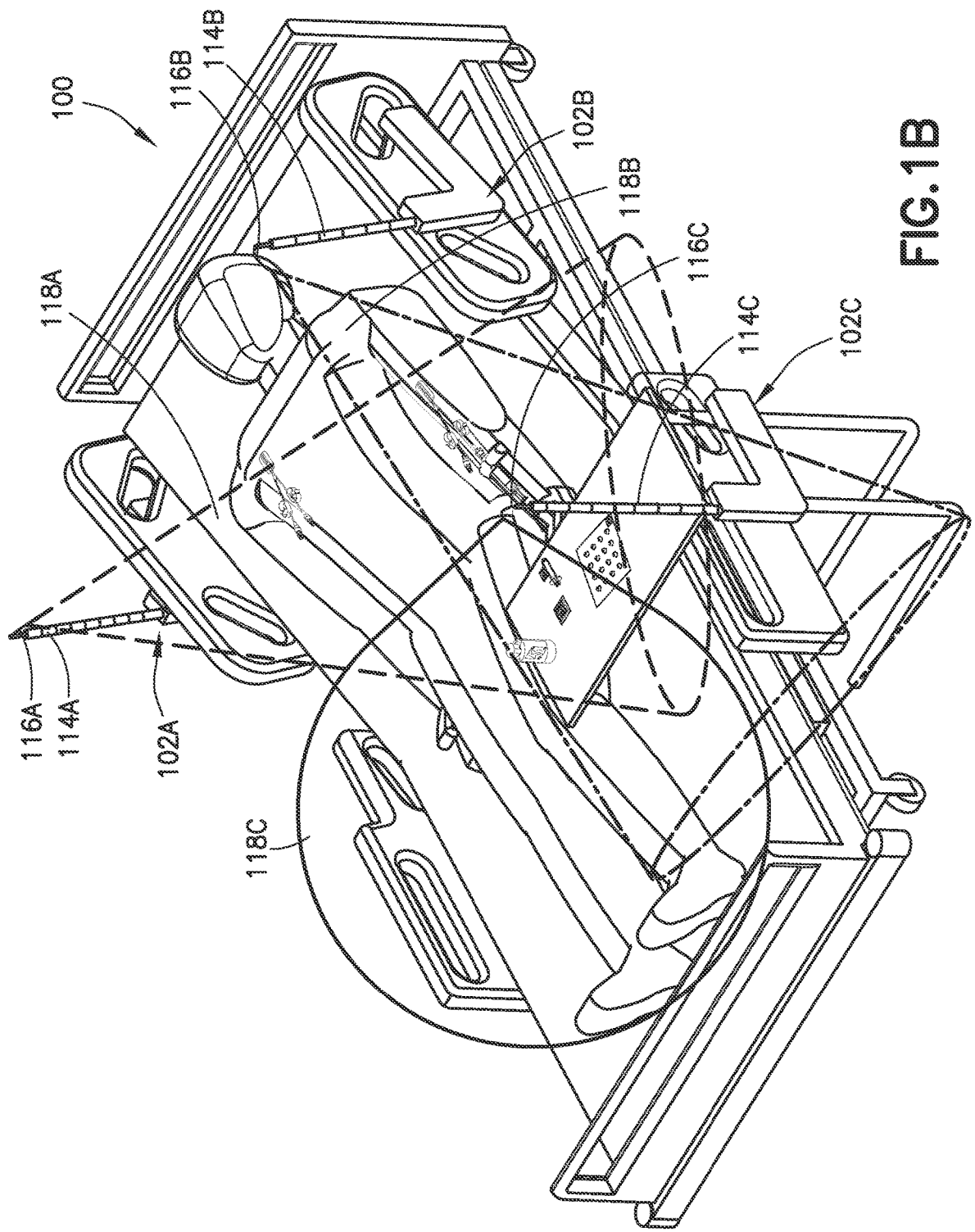

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

For purposes of the description hereinafter, the terms "end," "upper," "lower," "right," "left," "vertical," "horizontal," "top," "bottom," "lateral," "longitudinal," and derivatives thereof shall relate to embodiments or aspects as they are oriented in the drawing figures. However, it is to be understood that embodiments or aspects may assume various alternative variations and step sequences, except where expressly specified to the contrary. It is also to be understood that the specific devices and processes illustrated in the attached drawings, and described in the following specification, are simply non-limiting exemplary embodiments or aspects. Hence, specific dimensions and other physical characteristics related to the embodiments or aspects of the embodiments or aspects disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." As used in the specification and the claims, the singular form of "a," "an," and "the" include plural referents, such as unless the context clearly dictates otherwise. Additionally, Furthermore, as used herein, the terms "set" and "group" are intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise. Further, the phrase "based on" is intended to mean "based at least partially on" unless explicitly stated otherwise. Further, the phrase "based on" may mean "in response to" and be indicative of a condition for automatically triggering a specified operation of an electronic device (e.g., a controller, a processor, a computing device, etc.) as appropriately referred to herein.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or send (e.g., transmit) information to the other unit. This may refer to a direct or indirect connection that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located between the first unit and the second unit) processes information received from the first unit and transmits the processed information to the second unit. In some non-limiting embodiments or aspects, a message may refer to a network packet (e.g., a data packet and/or the like) that includes data.

Some non-limiting embodiments or aspects may be described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Embodiments of the present disclosure are directed to an improved adjustable image capture device. With this, embodiments of the present disclosure allow for obtaining information, for example, in the form of images, that may require adequate vantage angles for an image capture device. Embodiments of the present disclosure allow for obtaining the information even in situations where an object may be in a wide range of locations or orientations and where the object may need to be tracked, despite being moved to various locations, at various orientation angles, and with view blocking obstructions.

Figure 1C:
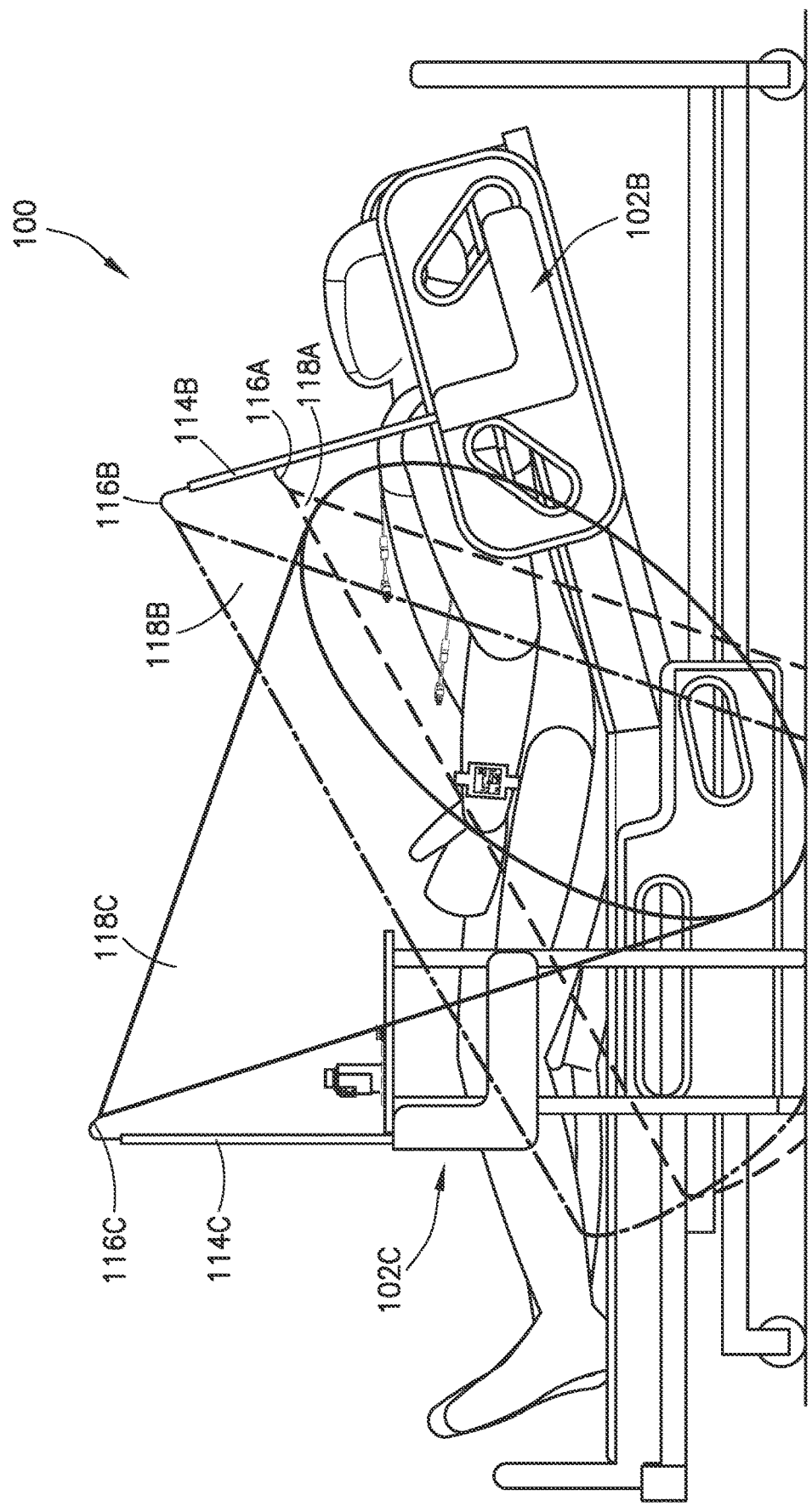
Figure 1D:
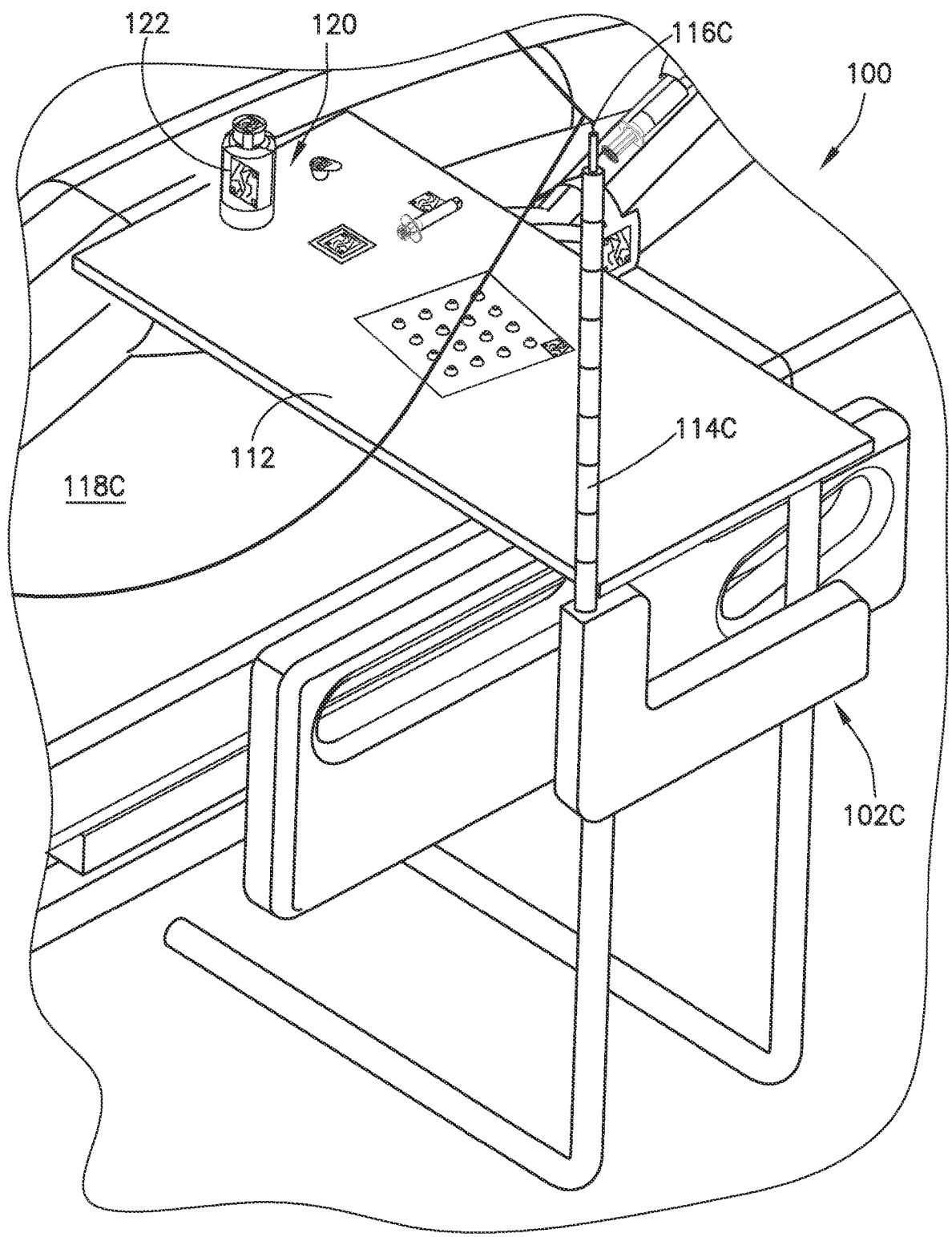

Referring now to FIGS. 1A-1E, FIGS. 1A-1E are diagrams of a non-limiting embodiment of implementation 100 of adjustable image capture device 102. As shown in FIGS. 1A-1E, implementation 100 may include a plurality of adjustable image capture devices 102A, 102B, 102C (referred individually as "adjustable image capture device 102" and collectively as "adjustable image capture devices 102" as appropriate). As further shown in FIGS. 1A-1E, the plurality of adjustable image capture devices 102A, 102B, and 102C may be attached at various locations on hospital bed 104. The plurality of adjustable image capture devices 102A, 102B, 102C may be positioned at the various locations of hospital bed 104 to capture images of various aspects of the environment and/or surroundings of hospital bed 104 and/or patient 106 that is situated in hospital bed 104. As further shown in FIGS. 1A-1E, adjustable image capture devices 102A may be attached (e.g., via fasteners, adhesives, clamps, etc.) to hospital bed rail 108. Further, adjustable image capture devices 102B may be attached to another hospital bed rail 108. In addition, adjustable image capture devices 102C may be attached to another hospital bed rail 108 to table rails 110 of hospital bed table 112. As shown in FIGS. 1A and 1D, adjustable image capture device 102C may be positioned in proximity to patient 106 and/or in proximity to hospital bed table 112 to capture an image of objects 120, which may contain medical supplies.

As shown in FIG. 1A, adjustable image capture devices 102-A, 102-B, 102-C may be in a first state. In the first states, a linkage assembly of a respective adjustable image capture device 102-A, 102-B, 102-C may be positioned inside a channel of a housing of a respective adjustable image capture device 102-A, 102-B, 102-C.

As shown in FIGS. 1B and 1C, adjustable image capture device 102 may be in a second state. In the second state, the linkage assembly of a respective adjustable image capture device 102-A, 102-B, 102-C may be positioned outside a channels of a housing of a respective adjustable image capture device 102-A, 102-B, 102-C. In some non-limiting embodiments, adjustable image capture devices 102-A, 102-B, 102-C may transition from a first state to a second state based on receiving command (e.g., an input, an instruction, etc., from a control system, such as a computer vision system that controls one or more adjustable image capture devices 102).

As shown in FIGS. 1B and 1C, image capture device 116A, 116B, 116C of a respective adjustable image capture device 102-A, 102-B, 102-C, may be positioned to capture an image of an environment and/or surroundings of hospital bed 104 and/or patient 106 that is within field of view 118A, 118B, 118C of a respective adjustable image capture device 102-A, 102-B, 102-C. In some non-limiting embodiments, field of view 118A, 118B, 118C of a respective adjustable image capture device 102-A, 102-B, 102-C may be adjusted based on movement of linkage assembly 114A, 114B, 114C of a respective adjustable image capture device 102-A, 102-B, 102-C. For example, field of view 118A, 118B, 118C of a respective adjustable image capture device 102-A, 102-B, 102-C may be adjusted based on transitioning linkage assembly 114A, 114B, 114C of a respective adjustable image capture device 102-A, 102-B, 102-C from a first state to a second state.

As shown in FIG. 1D, adjustable image capture device 102C may be in a second state, where one or more linkages of linkage assembly 114C are positioned outside of a channel of a housing of adjustable image capture device 102C. As further shown in FIG. 1D, image capture device 116C of adjustable image capture device 102C may be positioned to capture an image of an area of hospital bed table 112. The image may include an image of items located on hospital bed table 112, including objects 120. Object 120 may include medical supplies having an indicia, such as barcode 122. In some non-limiting embodiments, by capturing an image of medical supplies that includes barcode 122, a control system (e.g., a computer vision system) may be determine information regarding the medical supplies based on the information included in the image associated with barcode 122.

Figure 1E:
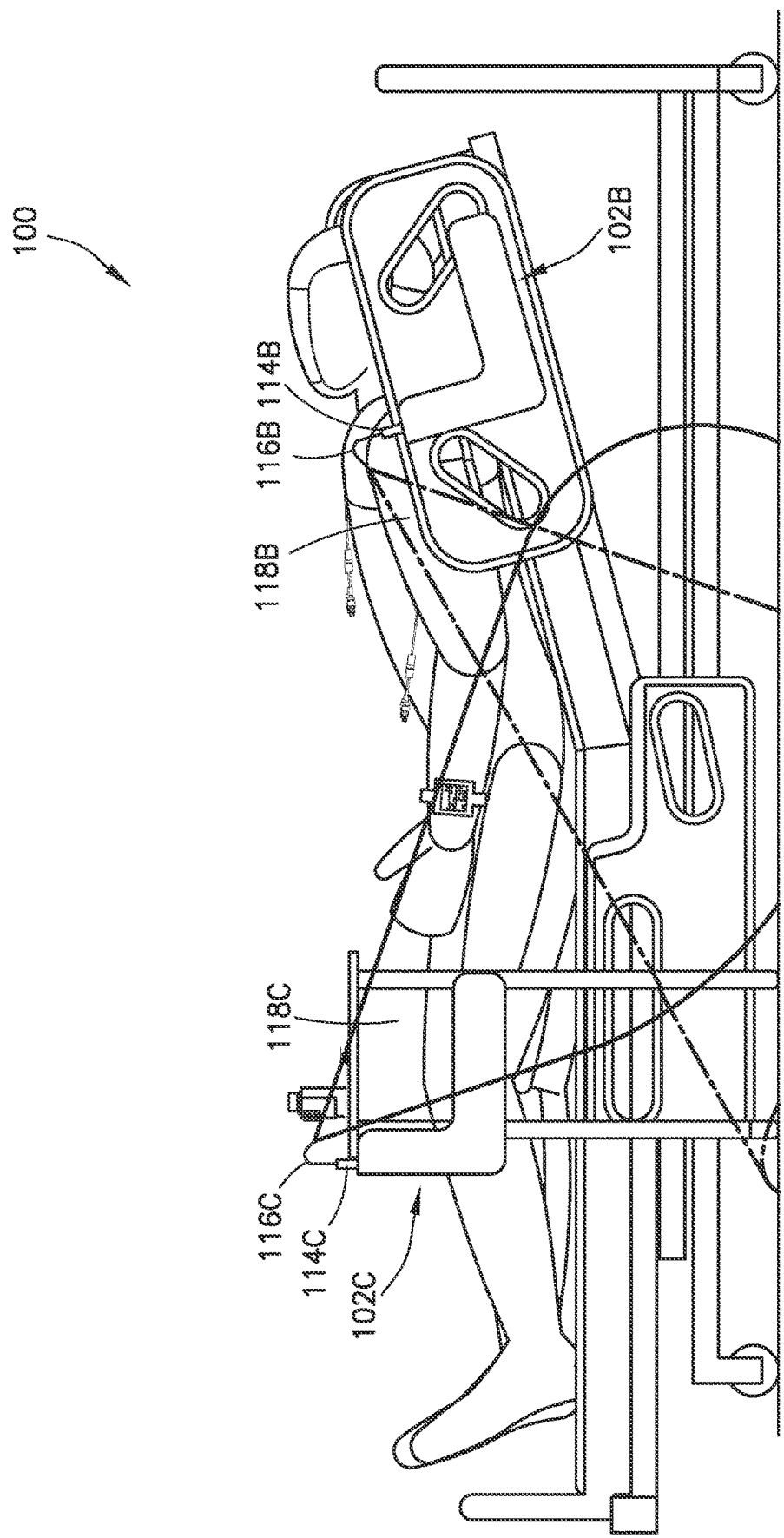

As shown in FIG. 1E, adjustable image capture devices 102-A, 102-B, 102-C may be in the first state after being in the second state, such that a linkage assembly of a respective adjustable image capture device 102-A, 102-B, 102-C may be positioned inside a channel of a housing of a respective adjustable image capture device 102-A, 102-B, 102-C. In some non-limiting embodiments, adjustable image capture devices 102-A, 102-B, 102-C may transition from a second state to a first state based on receiving command (e.g., an input, an instruction, etc., from a control system, such as a computer vision system that controls one or more adjustable image capture devices 102).

As further shown in FIG. 1E, image capture device 116A, 116B, 116C of a respective adjustable image capture device 102-A, 102-B, 102-C, may be positioned to capture an image of an environment and/or surroundings of hospital bed 104 and/or patient 106 that is within field of view 118A, 118B, 118C of a respective adjustable image capture device 102-A, 102-B, 102-C, when adjustable image capture devices 102-A, 102-B, 102-C are in the first state.

Figure 2A:
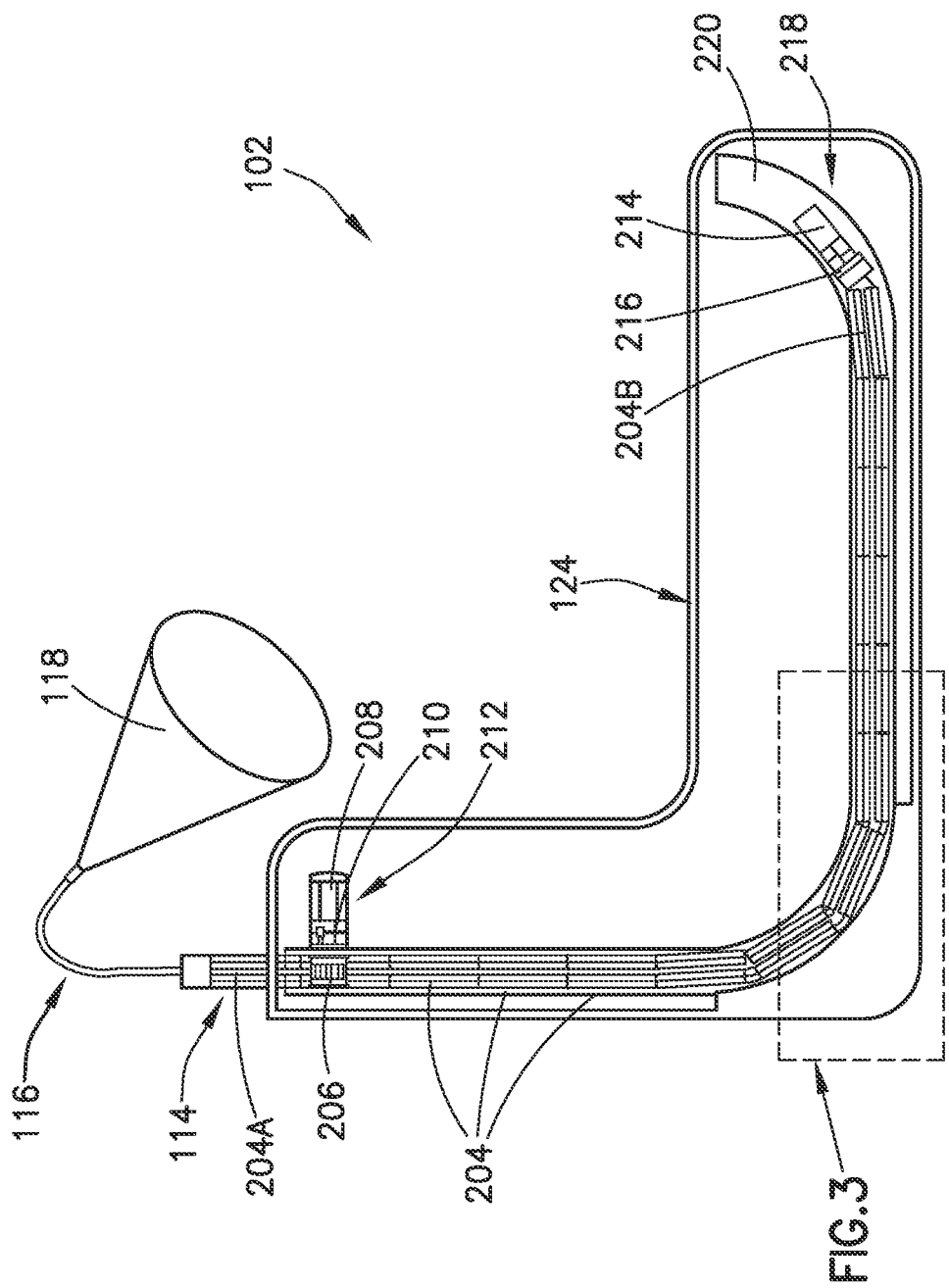
FIGS. 2A and 2B are diagrams of a non-limiting embodiment of an adjustable image capture device.
Figure 2B:
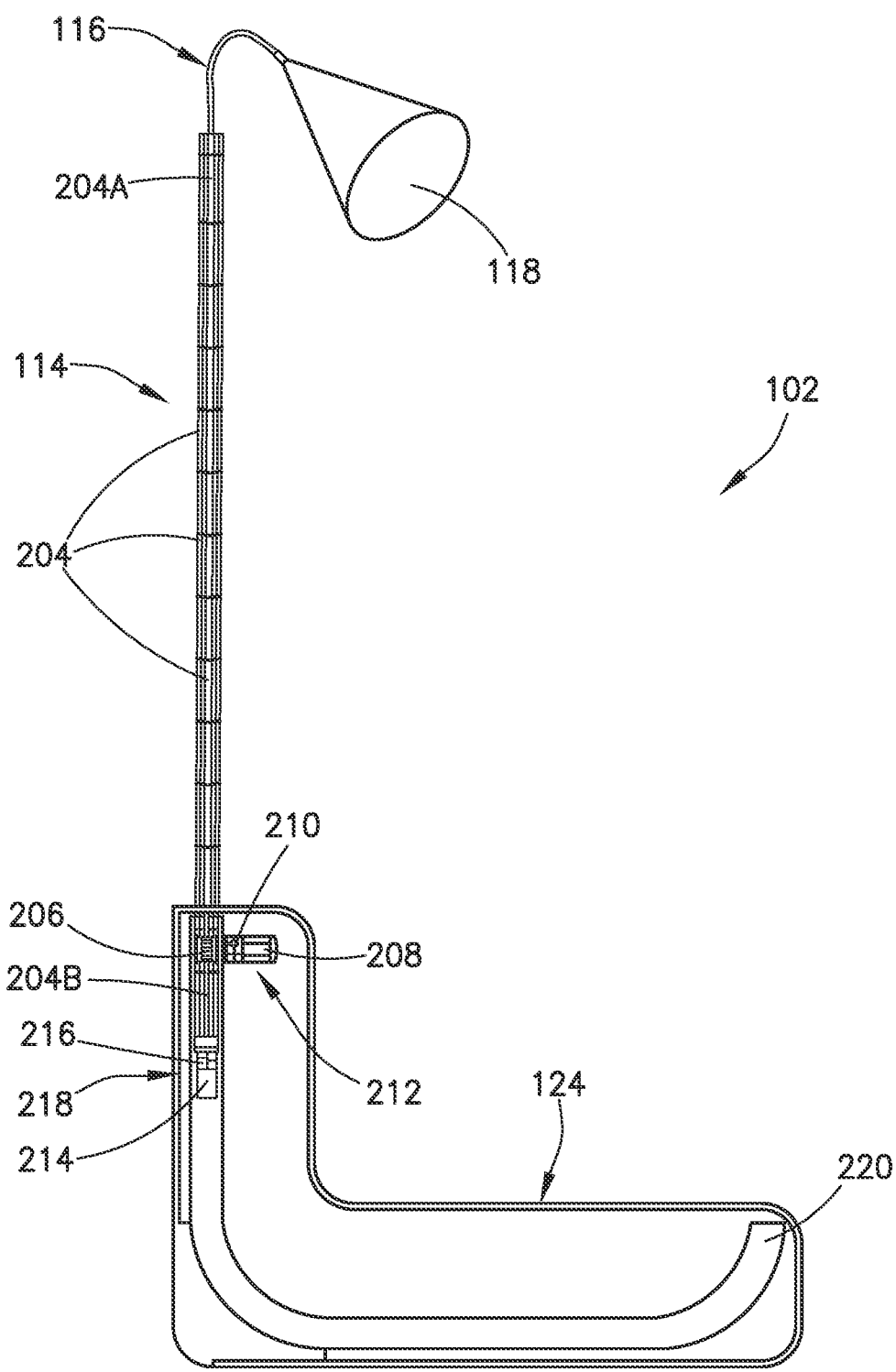

Referring now to FIGS. 2A and 2B, FIGS. 2A and 2B are diagrams of a non-limiting embodiment of adjustable image capture device 102. FIG. 2A is a diagram of linkage assembly 114 in a first state, where each linkage 204 of a plurality of linkages 204 of linkage assembly 114 are positioned inside channel 220 of housing 124. FIG. 2B is a diagram of linkage assembly 114 in a second state, where one or more linkages 204 of the plurality of linkages 204 of linkage assembly 114 are positioned outside channel 220 of housing 124.

As shown in FIGS. 2A and 2B, adjustable image capture device 102 may include housing 124, linkage assembly 114, and image capture device 116. In some non-limiting embodiments, housing 124 may have an L-shape. In some non-limiting embodiments, housing 124 may be configured to contain all electrical and mechanical components of adjustable image capture device 102 (e.g., electronics, lines, cords, cables, etc.).

In some non-limiting embodiments, linkage assembly 114 may include a plurality of linkages 204. In some non-limiting embodiments, the plurality of linkages 204 may include first end linkage 204A and second end linkage 204B. In some non-limiting embodiments, first end linkage 204A may be adjacent an opening of housing 124 when linkage assembly 114 is in a first state and/or may be positioned outside of housing 124 when linkage assembly 114 is in a second state. In some non-limiting embodiments, second end linkage 204B may be positioned inside of housing 124 when linkage assembly 114 is in first state or when linkage assembly 114 is in the second state.

In some non-limiting embodiments, when linkage assembly 114 is in a first state, first end linkage 204A of linkage assembly 114 may be positioned at least partially inside channel 220 of housing 124 or first end linkage 204A of linkage assembly 114 may be positioned at least partial outside channel 220 of housing 124.

In some non-limiting embodiments, linkage assembly 114 is configured to fit within housing 124. In some non-limiting embodiments, image capture device 116 may be configured to fit within linkage assembly 114 (e.g., within a bore of linkage assembly 114). In some non-limiting embodiments, linkage assembly 114 may be configured to fit within housing 124. For example, linkage assembly 114 may be configured to fit within channel 220 of housing 124.

In some non-limiting embodiments, image capture device 116 may include a camera that is sized and configured to fit within linkage assembly 114. For example, image capture device 116 may include a camera that is sized and configured to fit within a bore of linkage assembly 114. In some non-limiting embodiments, image capture device 116 may include a borescope camera. In some non-limiting embodiments, image capture device 116 may be configured such that field of view 118 is biased in a first direction. For example, image capture device 116 may have a curved shape such that field of view 118 is biased in a first direction, which is a direction that is angled way from linkage assembly 114. In some non-limiting embodiments, image capture device 116 may include power and/or signal lines for an image capture device (e.g., a camera). For example, image capture device 116 may include a tube structure that has power and/or signal lines for a camera placed at an end of the tube structure instead of a borescope camera.

As shown in FIGS. 2A and 2B, adjustable image capture device 102 may include extension motor assembly 212 and pan motor assembly 218. In some non-limiting embodiments, extension motor assembly 212 may include extension gear 206, extension motor 208, and extension motor support 210. In some non-limiting embodiments, extension gear 206 may include a gear that has teeth that mesh with teeth of a gear rack (e.g., a gear rack on each linkage 204 of the plurality of linkages 204 of linkage assembly 114), and extension motor 208 (e.g., a servo-motor) is configured to impart motion to extension gear 206, which causes linkage assembly 114 to extend away from housing 124 along a first axis (e.g., a longitudinal axis of linkage assembly 114, which may be defined by a bore of linkage assembly 114) or retract towards housing 124 along the first axis. In some non-limiting embodiments, extension motor assembly 212 may be positioned inside of channel 220 of housing 124. In some non-limiting embodiments, extension motor assembly 212 may be positioned outside of channel 220 of housing 124.

In some non-limiting embodiments, pan motor assembly 218 may include pan motor 214 and pan motor support 216. In some non-limiting embodiments, pan motor 214 (e.g., a servo-motor) may be coupled to (e.g., attached to via another component) the image capture device, and pan motor 214 may be configured to impart motion to image capture device 116. In some non-limiting embodiments, pan motor assembly 218 may be attached to linkage assembly 114. For example, pan motor assembly 218 may be attached to second end linkage 204B of linkage assembly 114. Additionally or alternatively, pan motor assembly 218 may be attached image capture device 116. In this way, pan motor 214 may be configured to impart motion (e.g., rotational motion) to image capture device 116 (e.g., field of view 118 of image capture device 116). In some non-limiting embodiments, pan motor assembly 218 may be configured to rotate a field of view 118 of image capture device 116 about a second axis (e.g., a second axis that is parallel to or coextensive with the first axis along which linkage assembly 114 may extend)

In some non-limiting embodiments, adjustable image capture device 102 may include a tilt motor assembly. Tilt motor assembly may include a tilt motor and a tilt motor support assembly and the tilt motor may be attached to image capture device 116. In some non-limiting embodiments, the tilt motor (e.g., a servo-motor) may be configured to impart motion to image capture device 116. In some non-limiting embodiments, the tilt motor assembly may be configured to rotate field of view 118 of image capture device 116 about a third axis which may be perpendicular to the second axis and/or the first axis.

In some non-limiting embodiments, when the tilt motor assembly is activated field of view 118 is adjusted from the first direction (e.g., a first direction to which field of view 118 of image capture device 116 is biased) to a second direction and there may be angle between the first direction and the second direction.

Figure 3:
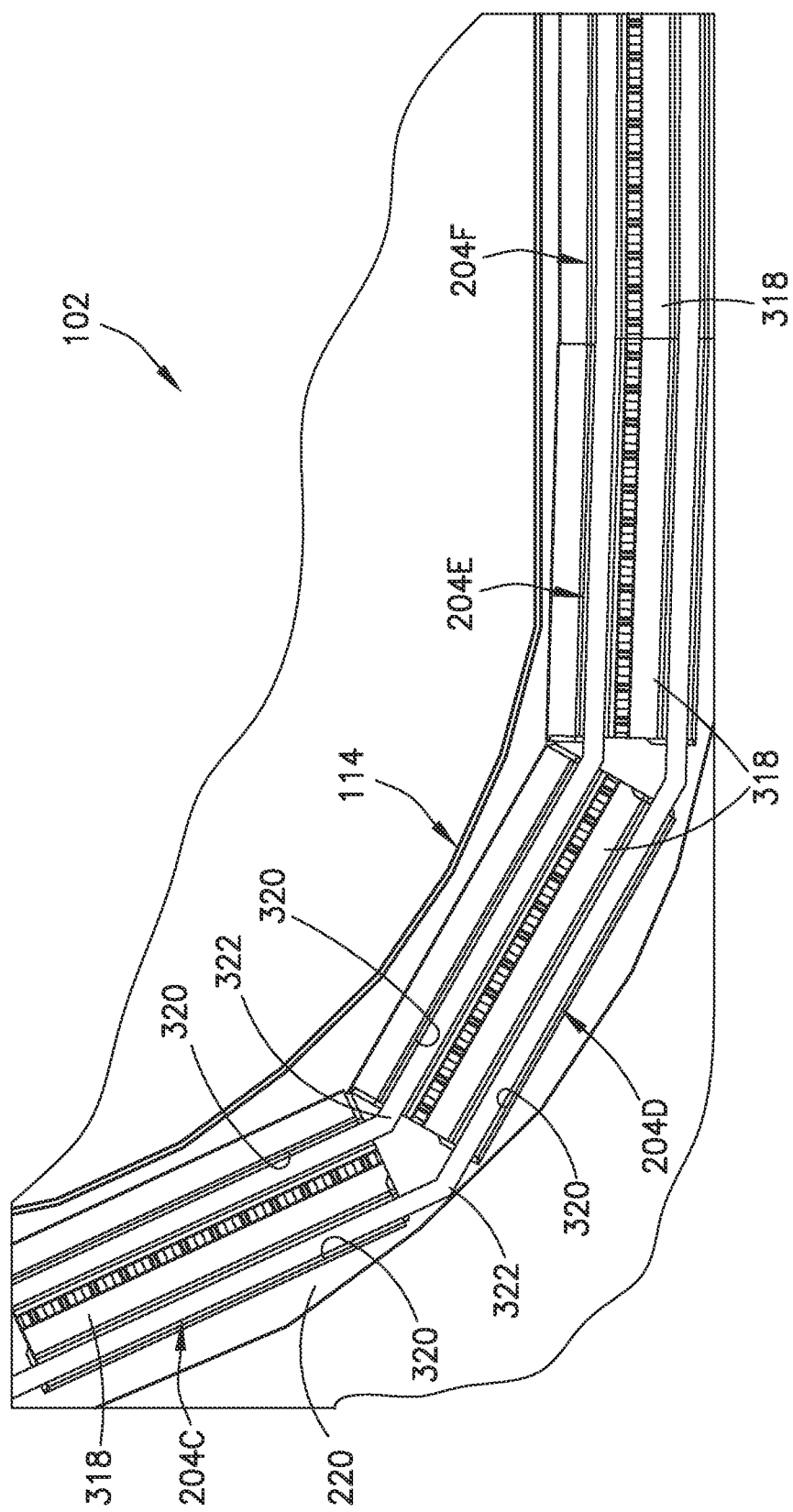
FIG. 3 is a diagram of a non-limiting embodiment of a linkage assembly of the adjustable image capture device shown in FIGS. 2A and 2B.

Referring now to FIG. 3, FIG. 3 is a diagram of a non-limiting embodiment of linkage assembly 114 of adjustable image capture device 102 shown in FIGS. 2A and 2B. As shown in FIG. 3, linkage assembly 114 may include a plurality of linkages 204 (e.g., a plurality of linkages 204, including first linkage 204C, second linkage 204D, third linkage 204E, and fourth linkage 204F) and each linkage 204 may have primary bore 318 and/or one or more secondary bores 320. Primary bore 318 may include a through-hole (e.g., a borehole, a center-hole, etc.) at a center of each linkage 204. Secondary bore may include a through-hole at a position that is off-center of each linkage 204. For example, each linkage may include a plurality of secondary bores 320 positioned adjacent and around primary bore 318. In such an example, plurality of secondary bores 320 may positioned symmetrically adjacent and symmetrically around primary bore 318 such that a center of each secondary bore 320 is equidistant from a center of primary bore 318.

As further shown in FIG. 3, linkage assembly 114 may be positioned within channel 220 of housing 124 and one or more linkages 204 of linkage assembly 114 may be in an unaligned state. In some non-limiting embodiments, linkages 204 of linkage assembly 114 may be in an unaligned state when primary bore 318 of a linkage 204 is not aligned with primary bore 318 of another linkage 204 and linkages 204 of linkage assembly 114 may be in an aligned state when primary bore 318 of a linkage 204 is aligned with primary bore 318 of another linkage 204. For example, as shown in FIG. 3, primary bore 318 of first linkage 204C is not aligned with primary bore 318 of second linkage 204D, and first linkage 204C is in an unaligned state with second linkage 204D. As further shown in FIG. 3, primary bore 318 of third linkage 204E is aligned with primary bore 318 of fourth linkage 204F, and third linkage 204E is in an aligned state with fourth linkage 204F.

In some non-limiting embodiments, linkage assembly 114 may have a central bore that is defined by primary bores 318 of linkages 204. In some non-limiting embodiments, image capture device 116 may be sized and configured to fit within the central bore of linkage assembly 114. In some non-limiting embodiments, linkage assembly 114 may be sized configured to fit within and conform to a shape of channel 220 of housing 124. For example, linkage assembly 114 may be sized configured such that linkages 204 of linkage assembly 114 are able to move (e.g., extend from and retract into) channel 220.

As further shown in FIG. 3, line 322 may be positioned within secondary bores 320 of each linkage 204. In some non-limiting embodiments, line 322 may include a material that is configured to hold linkages 204 in proximity when linkages 204 are an aligned state or in an unaligned state. For example, linkages 204 may be held in an aligned state based on tension of line 322 as linkage assembly 114 is extended from housing 124. In some non-limiting embodiments, line 322 may include an elastic material. In some non-limiting embodiments, line 322 may include a cord, a band, a string, and/or the like. As shown in FIG. 3, a first end of line 322 may be attached to first linkage 204C and a second end of line 322 may be attached to second linkage 204D. In some non-limiting embodiments, linkage assembly 114 may be configured to conform to a shape of channel 220 of housing 124 based on the tension of line 322. In some non-limiting embodiments, line 322 couples first linkage 204C to second linkage 204D.

Figure 4:
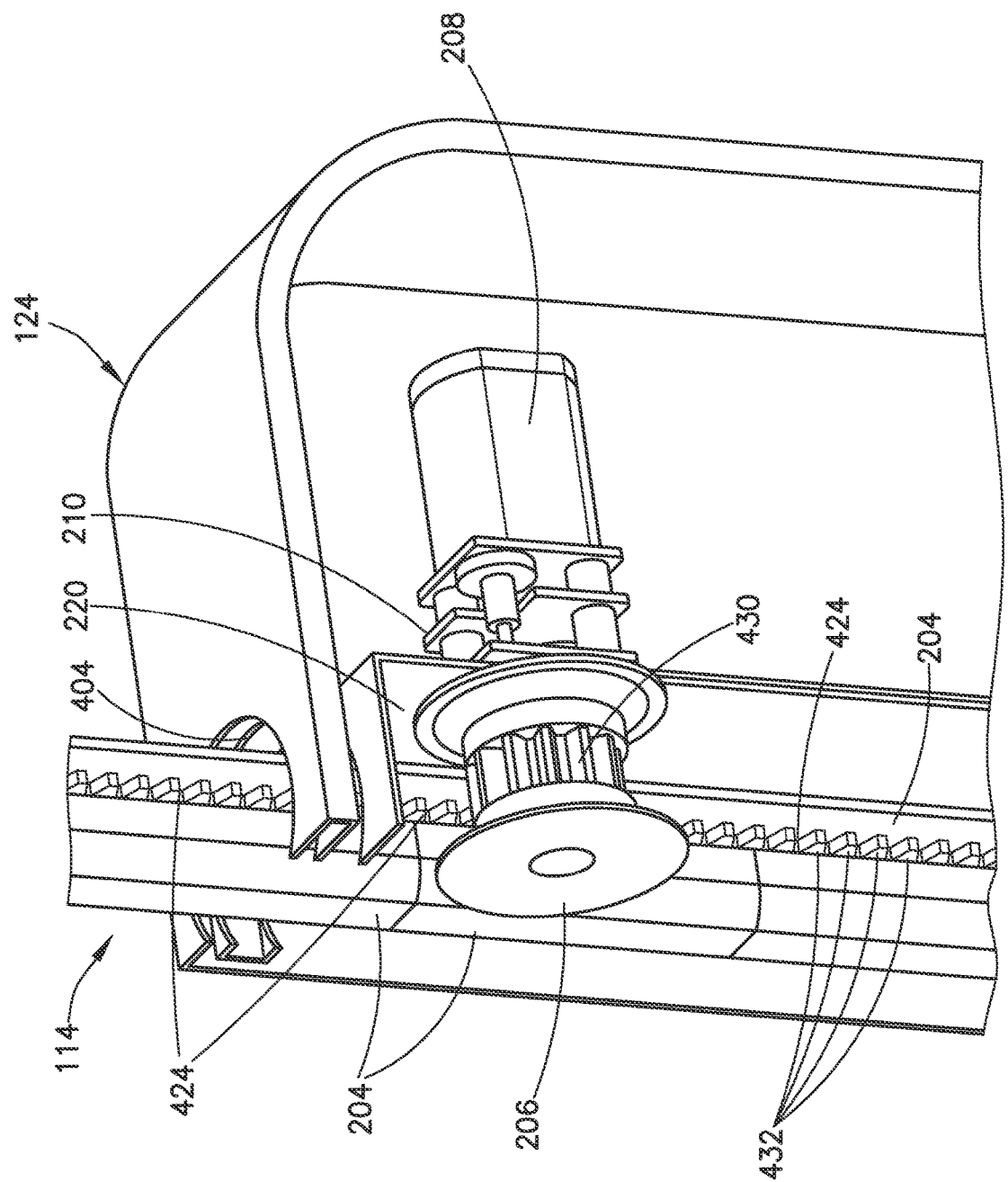
FIG. 4 is a diagram of a non-limiting embodiment of an extension motor assembly of the adjustable image capture device shown in FIGS. 2A and 2B.

Referring now to FIG. 4, FIG. 4 is a diagram of a non-limiting embodiment of extension motor assembly 212 of adjustable image capture device 102 shown in FIGS. 2A and 2B. As shown in FIG. 4, housing 124 may have opening 404 that provides access to channel 220, where linkages 204 of linkage assembly 114 are sized and configured to fit through opening 404. As further shown in FIG. 4, each linkage 204 of linkage assembly 114 may include gear rack 424 and each gear rack 424 may include gear rack teeth 432. As further shown in FIG. 4, extension gear 206 comprises extension gear teeth 430 which interact with gear rack teeth 432 of gear rack 224. In some non-limiting embodiments, extension motor assembly 212 is configured to transition linkage assembly 114 from the first state to the second state and vice versa.

In some non-limiting embodiments, extension gear teeth 430 of extension gear 206 may mesh with gear rack teeth 432 of gear rack 224 and extension motor 208 is configured to impart motion on linkage assembly 114 based on extension gear teeth 430 of extension gear 206 meshing with gear rack teeth 432 of gear rack 224. For example, extension motor 208 rotates extension gear 206, extension gear teeth 430 of extension gear 206 mesh with gear rack teeth 432 of gear rack 224 of linkages 204, which causes linkage assembly 114 to extend along a first axis. In this way, linkage assembly 114 may transition from the first state to the second state or from the second state to the first state.

In some non-limiting embodiments, the second state of linkage assembly 114 may include a plurality of sub-states. Each sub-state may define a position of linkage assembly 114 based on linkages 204 as they are positioned relative to housing 124 with regard to interaction of extension gear teeth 430 of extension gear 206 and gear rack teeth 432 of each gear rack 224. For example, as extension motor 208 rotates extension gear 206, extension gear teeth 430 of extension gear 206 mesh with gear rack teeth 432 of gear rack 224 of linkages 204, which causes each linkage 204 of linkage assembly 114 to move relative to housing 124 (e.g., extend along the first axis away from housing 124 and retract along the first axis toward housing 124). In this way, linkage assembly 114 may move incrementally in sub-states based on extension gear teeth 430 of extension gear 206 meshing with gear rack teeth 432 of gear rack 224 of linkages 204.

Figure 5:
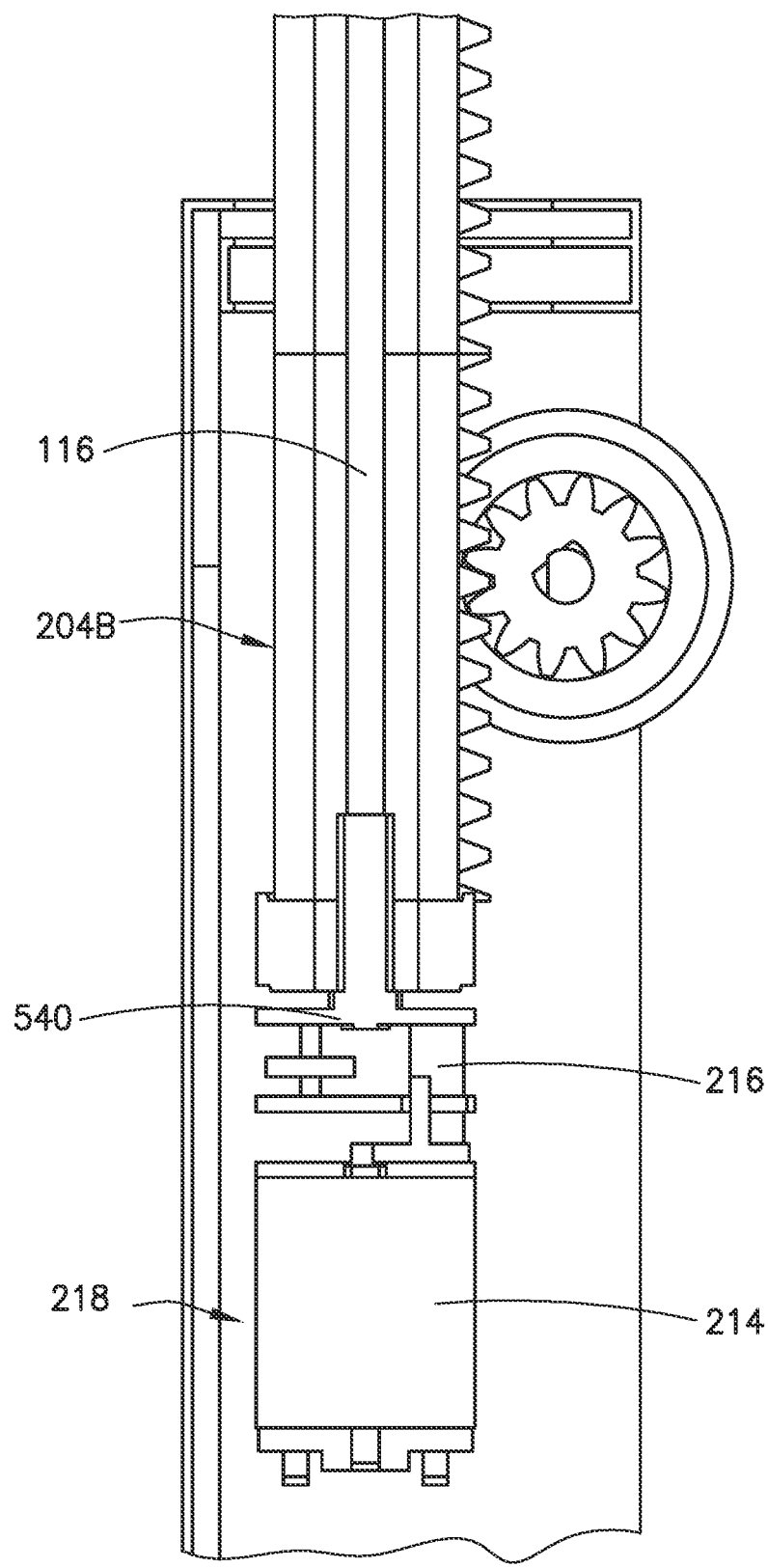
FIG. 5 is a diagram of a non-limiting embodiment of a pan motor assembly of the adjustable image capture device shown in FIGS. 2A and 2B.

Referring now to FIG. 5, FIG. 5 is a diagram of a non-limiting embodiment of pan motor assembly 218. As shown in FIG. 5, pan motor assembly 218 may include pan attachment 540. In some non-limiting embodiments, pan attachment 540 may include a component that attaches to image capture device 116 and pan motor support 216. In some non-limiting embodiments, pan motor assembly 218 may be attached to second end linkage 204B of linkage assembly 114 via pan attachment 540. In this way, pan motor 214 may be configured to impart motion (e.g., rotational motion) to image capture device 116 to rotate a field of view of image capture device 116 via pan attachment 540.

Figure 6:
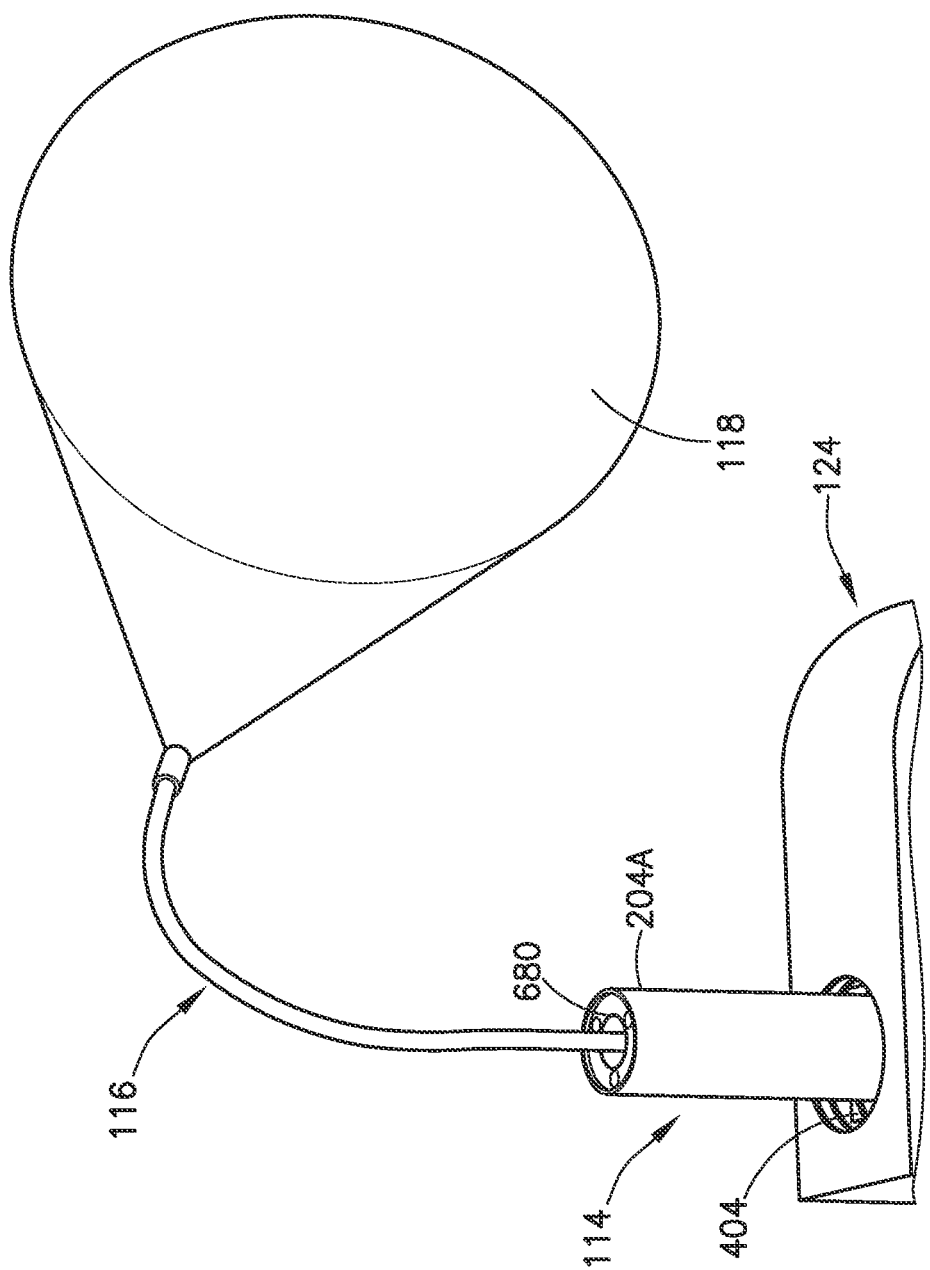
FIG. 6 is a diagram of a non-limiting embodiment of an image capture device of the adjustable image capture device shown in FIGS. 2A and 2B.

Referring now to FIG. 6, FIG. 6 is a diagram of a non-limiting embodiment of image capture device 116 of adjustable image capture device 102. As shown in FIG. 6, image capture device 116 may extend away from opening 404 of housing 124 based on linkage assembly 114 extending away from opening 404. In some non-limiting embodiments, image capture device 116 may be positioned in central bore 680 of linkage assembly 114, wherein central bore 680 is defined by a primary bore of each of the linkages of linkage assembly 114, including first end linkage 204A. As shown in FIG. 6, field of view 118 of image capture device 116 may be adjacent first end linkage 204A.

Figure 7A:
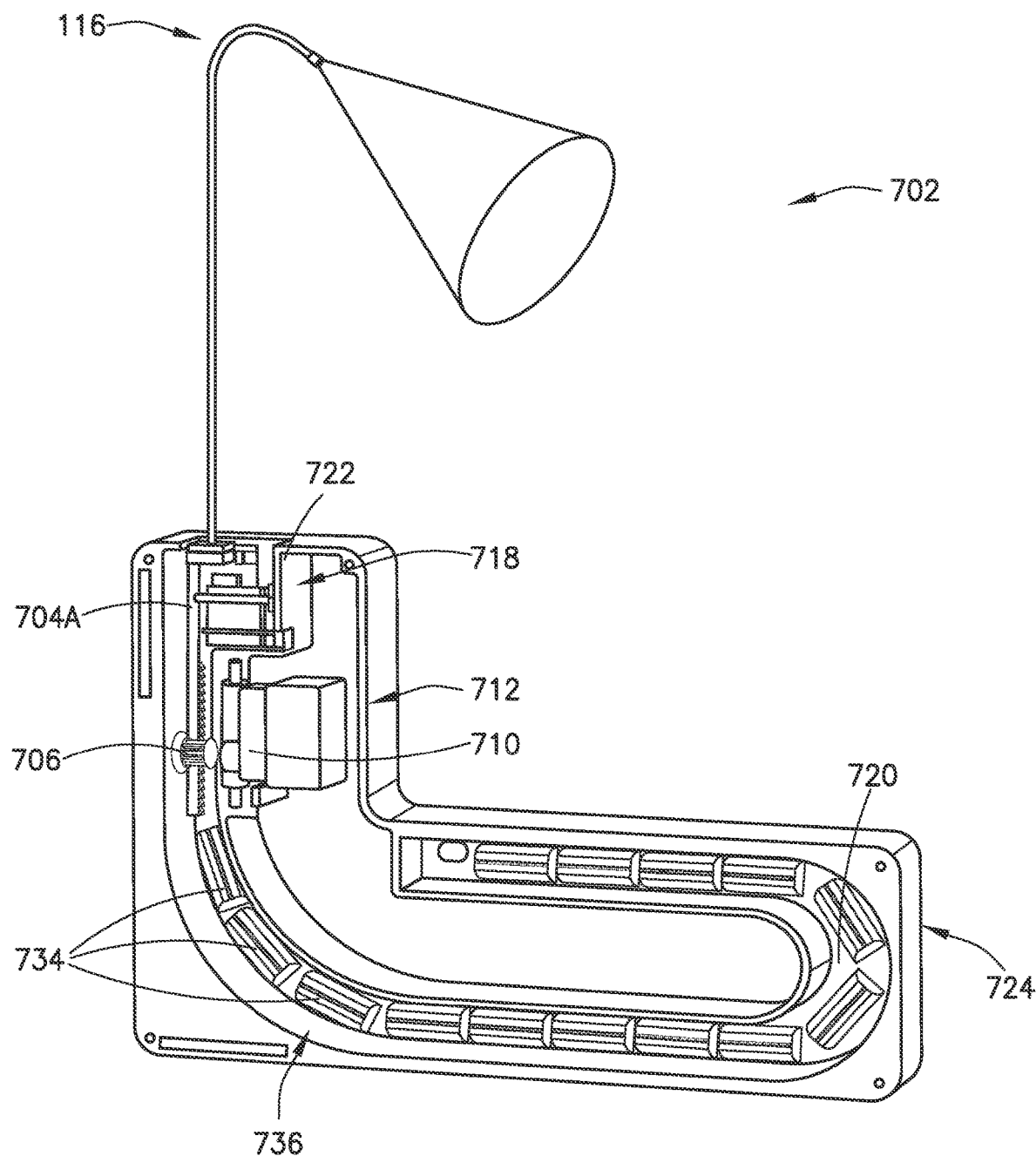
FIGS. 7A-7B are diagrams of a non-limiting embodiment of an adjustable image capture device.
Figure 7B:
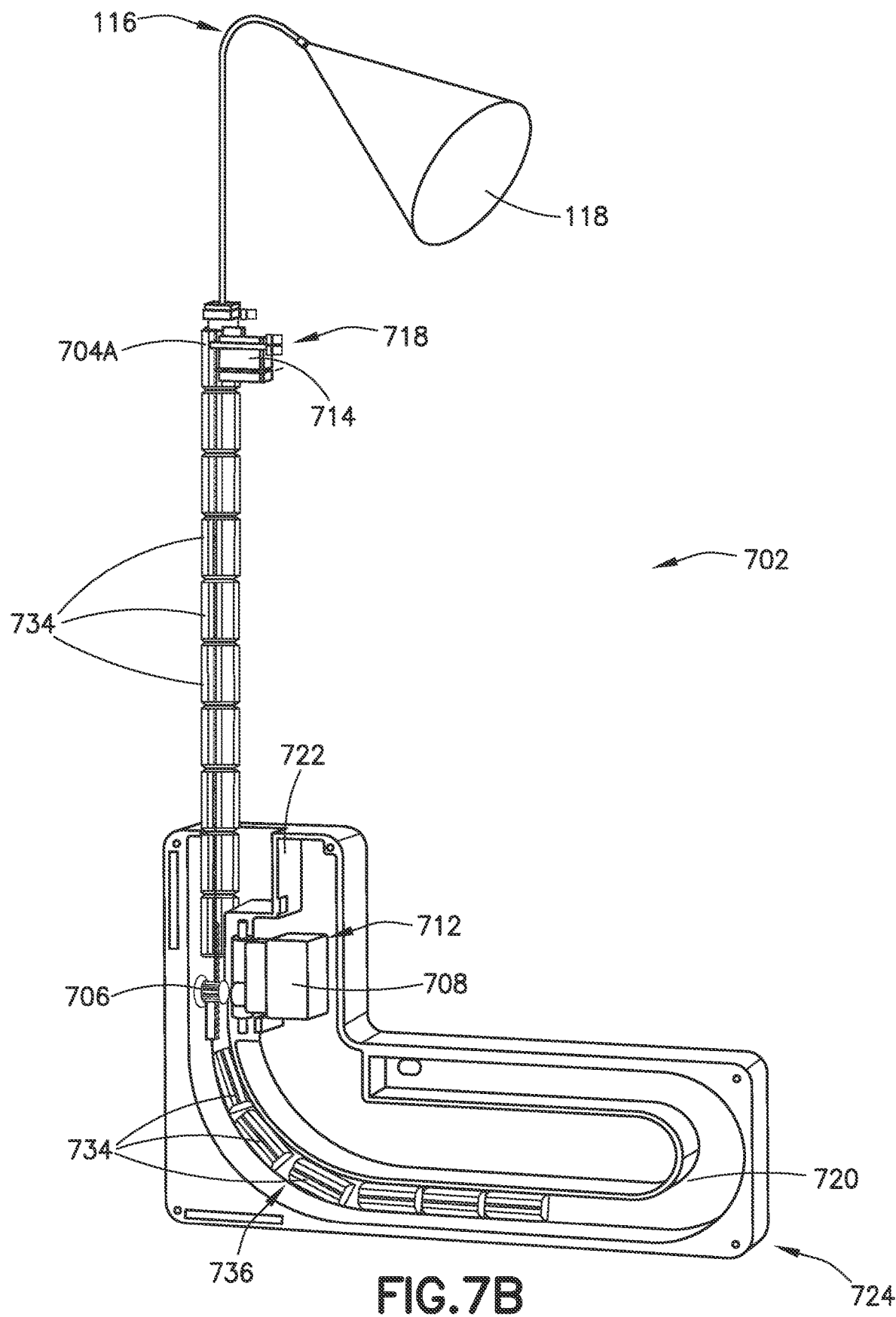

Referring now to FIGS. 7A and 7B, FIGS. 7A and 7B are diagrams of a non-limiting embodiment of adjustable image capture device 702. In some non-limiting embodiments, adjustable image capture device 702 may be the same or similar to adjustable image capture device 102.

As shown in FIGS. 7A and 7B adjustable image capture device 702 may include, extension motor assembly 712, pan motor assembly 718, linkage assembly 736, housing 724, and image capture device 116. In some non-limiting embodiments, extension motor assembly may be the same or similar to extension motor assembly 212. As further shown in FIGS. 7A and 7B, extension motor assembly 712 may include extension gear 706 and extension motor housing 708. In some non-limiting embodiments, extension gear 706 may be the same as or similar to extension gear 206. In some non-limiting embodiments, extension motor housing 710 may cover an extension motor.

In some non-limiting embodiments, housing 724 may be the same or similar to housing 124. As further shown in FIGS. 7A and 7B, housing 724 may include channel 720 and cavity 722. In some non-limiting embodiments, housing 724 may include an opening that is sized and configured to receive pan motor assembly 718, such that pan motor assembly 718 fits within cavity 722 when linkage assembly 726 is in the first state. In some non-limiting embodiments, channel 720 of housing 724 may have a first section that has a curved shape and a second section that has U-shape.

In some non-limiting embodiments, linkage assembly 736 may be the same as or similar to linkage assembly 114. As further shown in FIGS. 7A and 7B, linkage assembly 736 may include a plurality of linkages 734. In some non-limiting embodiments, the plurality of linkages 734 may include first end linkage 704A.

In some non-limiting embodiments, pan motor assembly 718 may be the same or similar to pan motor assembly 218. As further shown in FIGS. 7A and 7B, pan motor assembly 718 may be attached to first end linkage 704A.

Figure 8:
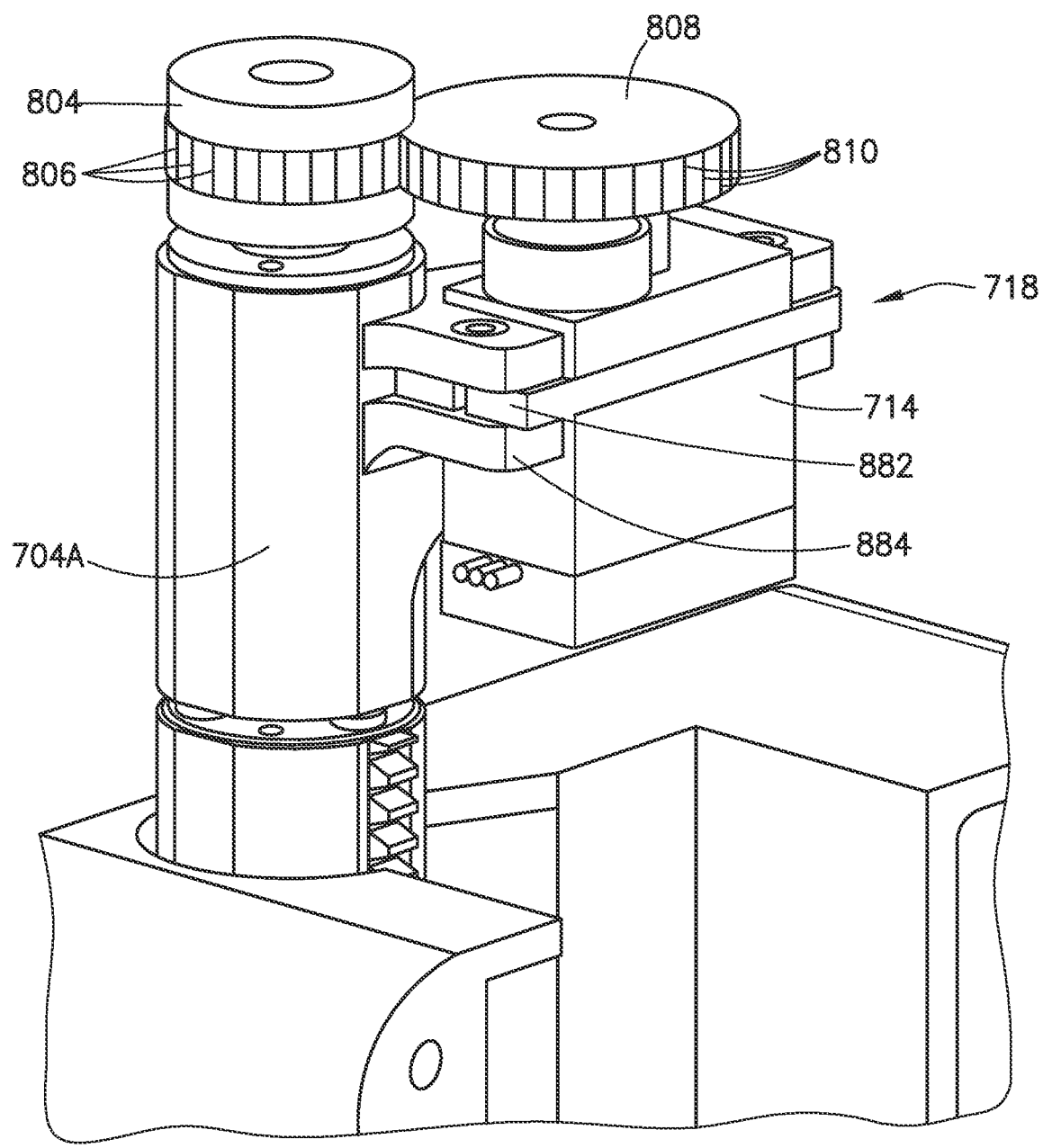
FIG. 8 is a diagram of a non-limiting embodiment of a pan motor assembly of the adjustable image capture device shown in FIGS. 7A-7B.

Referring now to FIG. 8, is a diagram of a non-limiting embodiment of a pan motor assembly 718 of adjustable image capture device 702 shown in FIGS. 7A-7B. In some non-limiting embodiments, pan motor assembly 718 may include first pan gear 804, second pan gear 808, pan motor housing 714, and flange 882. In some non-limiting embodiments, pan motor assembly 718 may attach to first end linkage 704A via bracket 884, of first end linkage 704A.

In some non-limiting embodiments, first pan gear 804 may include first gear teeth 806 and second pan gear 808 may include second gear teeth 810. As further shown in FIG. 8, first gear teeth 806 of first pan gear 804 may mesh with second gear teeth 810 of second pan gear 808 and pan motor assembly 718 is configured to impart motion on first pan gear 804 based on first gear teeth 806 meshing with second gear teeth 810 of second pan gear 808. For example, when pan motor assembly 718 rotates second pan gear 808, second gear teeth 810 of second pan gear 808 mesh with first gear teeth 806 of first pan gear 804, which causes image capture device to rotate, which rotate a field of view.

Figure 9A:
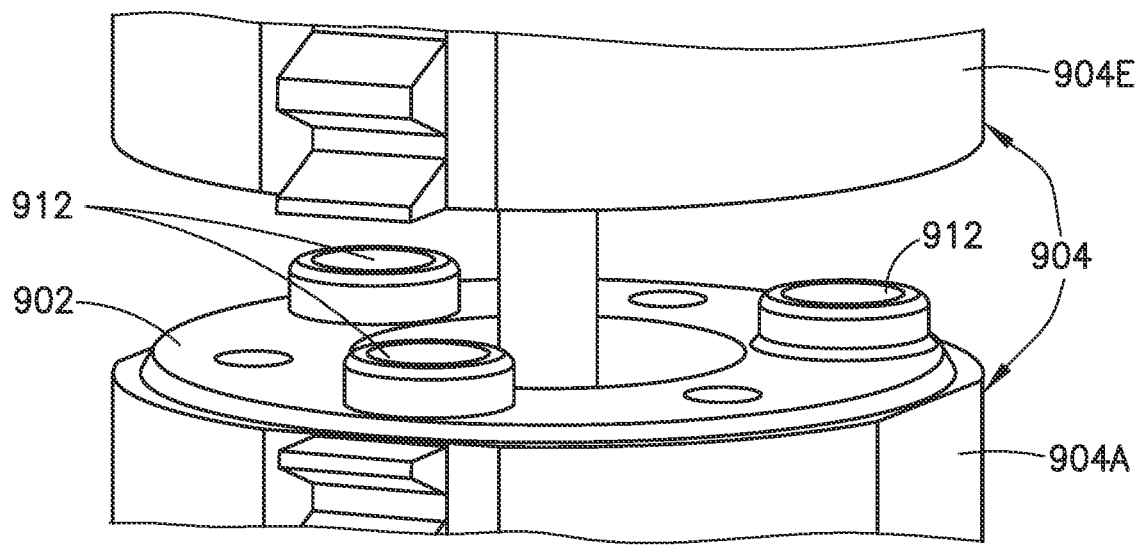
FIGS. 9A and 9B are diagrams of a non-limiting embodiment of linkages of the adjustable image capture device shown in FIGS. 7A-7B.
Figure 9B:
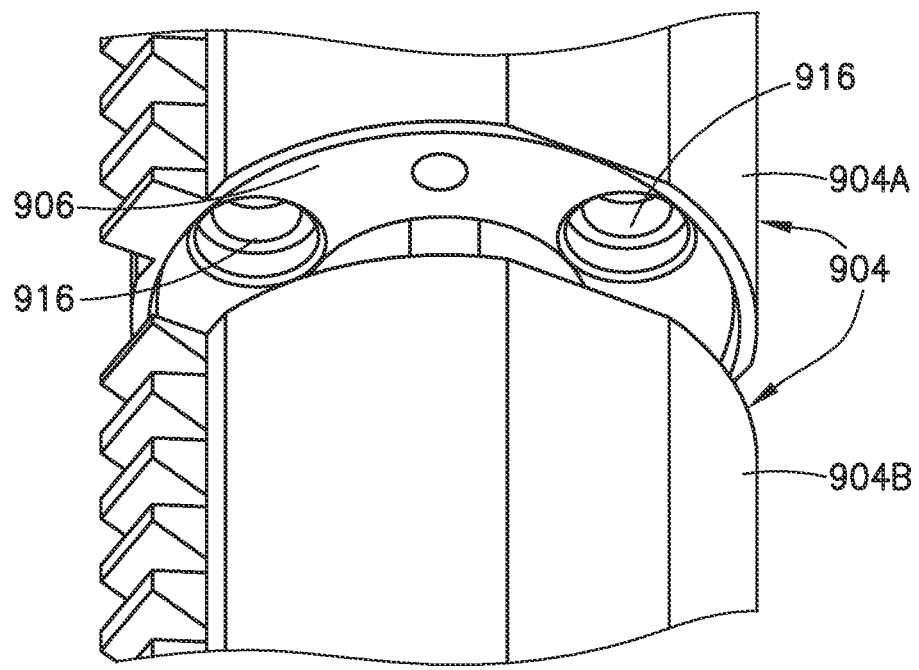

Referring now to FIGS. 9A, and 9B, FIGS. 9A and 9B are diagrams of a non-limiting embodiment of linkages 734 of adjustable image capture device 702 shown in FIGS. 7A-7B. In some non-limiting embodiments, linkages 904 may be the same or similar to linkages 704, which may be the same or similar to linkages 204.

As shown in FIGS. 9A and 9B, linkages 904 may include first linkage 904A and second linkage 904B. First linkage 904A may have first surface 902, where the first surface may include at least one magnet. In some non-limiting embodiments, second linkage 904B may have second surface 906, where second surface may include material that is attracted to the magnet positioned on first surface 902 of first linkage 904A.

As further shown in FIGS. 9A and 9B, first linkage 904A and second linkage 904B may be configured such that when second surface 906 of second linkage 904B is held in contact with first surface 902 first linkage 904A, the at least one magnet is attracted to the material of second surface 906, and first linkage 904A and second linkage 904B are in an aligned state.

In some non-limiting embodiments, first surface 902 of first linkage 904A may include at least one protrusion 912, and at least one protrusion 912 may include the at least one magnet. As further shown in FIGS. 9A and 9B second surface 906 of second linkage 904B may include at least one recess 916, and at least one recess 916 may be sized and configured to receive at least one protrusion 912 of first surface 902, and at least one recess 916 may be configured such that when at least one recess 916 receives at least one protrusion 912, first linkage 904A and second linkage 904B are in an aligned state.

In some non-limiting embodiments, at least one magnet positioned on first surface 902 may be at least one first magnet, where at least one recess 916 of second surface 906 may include at least one second magnet, and at least one first magnet may be configured to be attracted to at least one second magnet.

Figure 10:
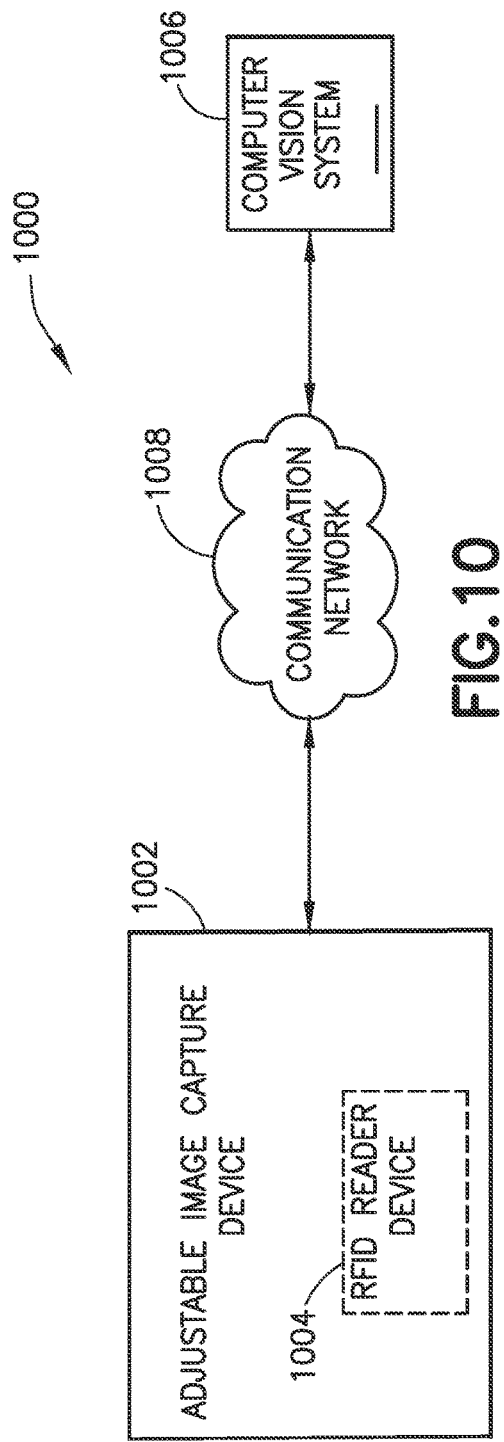
FIG. 10 is a diagram of a non-limiting embodiment or aspect of a technical environment in which methods, systems, and/or computer program products, described herein, may be implemented according to the principles of the presently disclosed subject matter.

Referring now to FIG. 10, FIG. 10 is a diagram of a non-limiting embodiment or aspect of technical environment 1000 in which systems, computer program products, and/or methods, as described herein, may be implemented. As shown in FIG. 10, technical environment 1000 includes adjustable image capture device 1002, computer vision system 1006, and communication network 1008. Adjustable image capture device 1002 and computer vision system 1006 may interconnect (e.g., establish a connection to communicate) via wired connections, wireless connections, or a combination of wired and wireless connections.

In some non-limiting embodiments, adjustable image capture device 1002 may be configured to capture one or more images of an environment and/or surroundings of particular location, such as a hospital bed and/or a patient and transmit data associated with the one or more images to computer vision system 1006 via communication network 1008. In some non-limiting embodiments, computer vision system 1006 may receive data associated with one or images captured by adjustable image capture device 1002 and computer vision system 1006 may use computer vision techniques to determine information based on the one or images. In some non-limiting embodiments, adjustable image capture device 1002 may be the same or similar to adjustable image capture device 102 and/or adjustable image capture device 702.

In some non-limiting embodiments, adjustable image capture device 1002 may include a device that is capable of being in communication with computer vision system 1006. In some non-limiting embodiments, adjustable image capture device 1002 may include a device controller (e.g., a microcontroller), a processor, an integrated circuit, and/or the like. In some non-limiting embodiments, computer vision system 1006 may provide commands (e.g., instructions, signals, etc.) to adjustable image capture device 1002 to cause adjustable image capture device 1002 to transition from a first state to a second state. In some non-limiting embodiments, adjustable image capture device 1002 may include RFID reader device 1004. In some non-limiting embodiments, RFID reader device 1004 may be a separate component from adjustable image capture device 1002. In some non-limiting embodiments, RFID reader device 1004 may be positioned on an image capture device (e.g., image capture device 116) of adjustable image capture device 1002. In some non-limiting embodiments, RFID reader device 1004 may replace an image capture device (e.g., image capture device 116) of adjustable image capture device 1002.

RFID reader device 1004 may include one or more devices configured to be in communication with an RFID tag. For example, RFID reader device 1004 may include one or more RFID readers (e.g., a device that includes a radio frequency (RF) transmitter and an RF receiver that is capable of reading and/or writing information to an RFID tag). In some non-limiting embodiments, RFID reader device 1004 may include one or more devices configured to be in communication (e.g., wired or wireless) with a device or system via communication network 1008.

Computer vision system 1006 may include one or more devices configured to communicate with adjustable image capture device 1002 via communication network 1008. For example, computer vision system 1006 may include a computer, a server, a group of servers, and/or other like devices. In some non-limiting embodiments, computer vision system 1006 may be a component of adjustable image capture device 1002. In some non-limiting embodiments or aspects, computer vision system 1006 may be in communication with a data storage device, which may be local or remote to computer vision system 1006. In some non-limiting embodiments or aspects, computer vision system 1006 may be capable of receiving information from, storing information in, transmitting information to, and/or searching information stored in the data storage device.

Communication network 1008 may include one or more wired and/or wireless networks. For example, communication network 1008 may include a cellular network (e.g., a long-term evolution (LTE) network, a third generation (3G) network, a fourth generation (4G) network, a fifth generation (5G) network, a code division multiple access (CDMA) network, and/or the like), a public land mobile network (PLMN), a local area network (LAN), a wide area network (WAN), a metropolitan area network (MAN), a telephone network (e.g., the public switched telephone network (PSTN)), a private network (e.g., a private network associated with a transaction service provider), an ad hoc network, an intranet, the Internet, a fiber optic-based network, a cloud computing network, and/or the like, and/or a combination of these or other types of networks.

Figure 11:
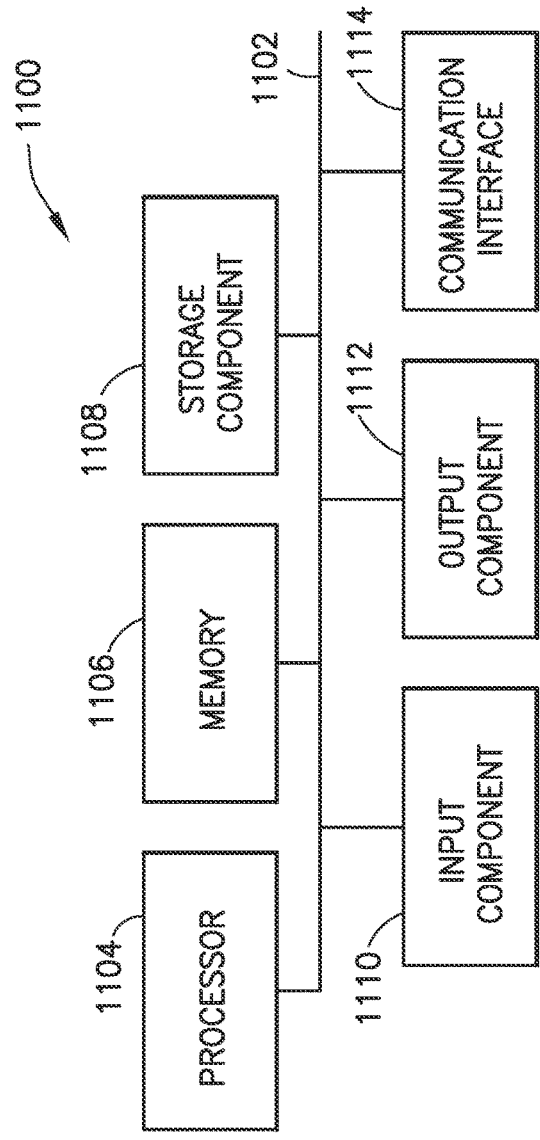
FIG. 11 is a diagram of a non-limiting embodiment of components of one or more devices and/or one or more systems of FIG. 10.

Referring now to FIG. 11, FIG. 11 is a diagram of example components of device 1100. Device 1100 may correspond to adjustable image capture device 1002, RFID reader device 1004, and/or computer vision system 1006. In some non-limiting embodiments, image capture device 1002, RFID reader device 1004, and/or computer vision system 1006 may include at least one device 1100 and/or at least one component of device 1100. As shown in FIG. 11, device 1100 may include bus 1102, processor 1104, memory 1106, storage component 1108, input component 1110, output component 1112, and communication interface 1114.

Bus 1102 may include a component that permits communication among the components of device 1100. In some non-limiting embodiments or aspects, processor 1104 may be implemented in hardware, software, or a combination of hardware and software. For example, processor 1104 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 1106 may include random access memory (RAM), read-only memory (ROM), and/or another type of dynamic or static storage device (e.g., flash memory, magnetic memory, optical memory, etc.) that stores information and/or instructions for use by processor 1104.

Storage component 1108 may store information and/or software related to the operation and use of device 1100. For example, storage component 1108 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 1110 may include a component that permits device 1100 to receive information, such as via user input (e.g., a touchscreen display, a keyboard, a keypad, a mouse, a button, a switch, a microphone, a camera, etc.). Additionally or alternatively, input component 1110 may include a sensor for sensing information (e.g., a global positioning system (GPS) component, an accelerometer, a gyroscope, an actuator, etc.). Output component 1112 may include a component that provides output information from device 1100 (e.g., a display, a speaker, one or more light-emitting diodes (LEDs), etc.).

Communication interface 1114 may include a transceiver-like component (e.g., a transceiver, a separate receiver and transmitter, etc.) that enables device 1100 to communicate with other devices, such as via a wired connection, a wireless connection, or a combination of wired and wireless connections. Communication interface 1114 may permit device 1100 to receive information from another device and/or provide information to another device. For example, communication interface 1114 may include an Ethernet interface, an optical interface, a coaxial interface, an infrared interface, a radio frequency (RF) interface, a universal serial bus (USB) interface, a Wi-Fi® interface, a Bluetooth® interface, a Zigbee® interface, a cellular network interface, and/or the like.

Device 1100 may perform one or more processes described herein. Device 1100 may perform these processes based on processor 1104 executing software instructions stored by a computer-readable medium, such as memory 1106 and/or storage component 1108. A computer-readable medium (e.g., a non-transitory computer-readable medium) is defined herein as a non-transitory memory device. A non-transitory memory device includes memory space located inside of a single physical storage device or memory space spread across multiple physical storage devices.

Software instructions may be read into memory 1106 and/or storage component 1108 from another computer-readable medium or from another device via communication interface 1114. When executed, software instructions stored in memory 1106 and/or storage component 1108 may cause processor 1104 to perform one or more processes described herein. Additionally or alternatively, hardwired circuitry may be used in place of or in combination with software instructions to perform one or more processes described herein. Thus, embodiments or aspects described herein are not limited to any specific combination of hardware circuitry and software.

Memory 1106 and/or storage component 1108 may include data storage or one or more data structures (e.g., a database and/or the like). Device 1100 may be capable of receiving information from, storing information in, communicating information to, or searching information stored in the data storage or one or more data structures in memory 1106 and/or storage component 1108. For example, the information may include input data, input data, output data, transaction data, account data, or any combination thereof.

The number and arrangement of components shown in FIG. 11 are provided as an example. In some non-limiting embodiments or aspects, device 1100 may include additional components, fewer components, different components, or differently arranged components than those shown in FIG. 11. Additionally or alternatively, a set of components (e.g., one or more components) of device 1100 may perform one or more functions described as being performed by another set of components of device 1100.

Although embodiments or aspects have been described in detail for the purpose of illustration and description, it is to be understood that such detail is solely for that purpose and that embodiments or aspects are not limited to the disclosed embodiments or aspects, but, on the contrary, are intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect. In fact, many of these features can be combined in ways not specifically recited in the claims and/or disclosed in the specification. Although each dependent claim listed below may directly depend on only one claim, the disclosure of possible implementations includes each dependent claim in combination with every other claim in the claim set.

What is claimed is:

1. An adjustable image capture device comprising:
a housing;
a linkage assembly, the linkage assembly having a bore, the linkage assembly comprising a plurality of linkages, and wherein each linkage having a bore, wherein the bores of the plurality of linkages defining the bore of the linkage assembly;
a motor fixed to the housing; and
an image capture device, wherein the image capture device is configured to fit within a bore of the linkage assembly;
wherein the linkage assembly is configured to fit within the housing;
wherein, when the linkage assembly is in a first state, each linkage of the plurality of linkages are positioned inside a channel of the housing;

wherein, when the linkage assembly is in a second state, one or more of the linkages of the plurality of linkages are positioned outside the channel of the housing; and wherein the motor is configured to impart motion to the linkage assembly to move the linkage assembly relative to the motor and to transition the linkage assembly from the first state to the second state.

2. The adjustable image capture device of claim 1, further comprising:
a pan motor assembly, wherein the pan motor assembly comprises:
a motor; and
wherein the motor is attached to the image capture device, and wherein the motor is configured to impart motion to the image capture device.

3. The adjustable image capture device of claim 1, wherein each linkage of the plurality of linkages has a gear rack, wherein the adjustable image capture device further comprises:
an extension motor assembly, wherein the extension motor assembly comprises:
a gear; and
the motor;
wherein the gear has teeth that mesh with teeth of the gear rack, and wherein the motor is configured to impart motion to the gear;
wherein the extension motor assembly is configured to extend the linkage assembly along a first axis.

4. The adjustable image capture device of claim 1, further comprising:
a tilt motor assembly, wherein the tilt motor assembly comprises:
a motor; and
wherein the motor is attached to the image capture device, and wherein the motor is configured to impart motion to the image capture device.

5. The adjustable image capture device of claim 1, wherein the housing has an opening that provides access the channel, and wherein the linkages of the linkage assembly are configured to fit through the opening.

6. The adjustable image capture device of claim 1, wherein the bore of a linkage is a primary bore, wherein the plurality of linkages comprises a first linkage and a second linkage;
wherein the first linkage has one or more secondary bores and the second linkage has one or more secondary bores;
wherein the one or more secondary bores of the first linkage are adjacent the primary bore of the first linkage, wherein the one or more secondary bores of the second linkage are adjacent the primary bore of the second linkage;
wherein a line is positioned in the one or more secondary bores of the first linkage and is positioned in the one or more secondary bores of the second linkage, wherein the line couples the first linkage to the second linkage.

7. The adjustable image capture device of claim 1, wherein the image capture device is a borescope camera.

8. The adjustable image capture device of claim 1, wherein the plurality of linkages comprises a first linkage and a second linkage, wherein the first linkage has a first surface, wherein the first surface comprises at least one magnet; and
wherein the second linkage has a second surface, wherein the second surface comprises a material that is attracted to the magnet positioned on the first surface of the first linkage.

9. The adjustable image capture device of claim 8, wherein the first linkage and the second linkage are configured such that when the second surface of the second linkage is held in contact with the first surface of the first linkage based on the at least one magnet being attracted to the material of the second surface, the first linkage and the second linkage are in an aligned state.

10. The adjustable image capture device of claim 9, wherein the first surface of the first linkage comprises at least one protrusion, and wherein the at least one protrusion comprises the at least one magnet.

11. The adjustable image capture device of claim 10, wherein the second surface of the second linkage comprises at least one recess, wherein the at least one recess is sized and configured to receive the at least one protrusion of the first surface; and
wherein the at least one recess is configured such that when the at least one recess receives the at least one protrusion, the first linkage and the second linkage are in an aligned state.

12. The adjustable image capture device of claim 11, wherein the at least one magnet positioned on the first surface is at least one first magnet, wherein at least one recess of the second surface comprises at least one second magnet, wherein the at least one first magnet is configured to be attracted to the at least one second magnet.

13. The adjustable image capture device of claim 12, further comprising:
a pan motor assembly, wherein the pan motor assembly comprises:
a motor; and
wherein the motor is coupled to the image capture device, and wherein the motor is configured to impart motion to the image capture device.

14. The adjustable image capture device of claim 13, wherein the linkage assembly comprises a first end and a second end, wherein the first end of the linkage assembly is adjacent an opening of the housing when the linkage assembly is in the first state; and
wherein the pan motor assembly is attached to the linkage assembly adjacent the first end of the linkage assembly.

15. The adjustable image capture device of claim 13, wherein each linkage of the plurality of linkages has a gear rack, the adjustable image capture device further comprising:
an extension motor assembly, wherein the extension motor assembly comprises:
a gear; and
a motor;
wherein the gear has teeth that mesh with teeth of the gear rack, and wherein the motor is configured to impart motion to the gear;
wherein the extension motor assembly is configured to extend the linkage assembly along a first axis;
wherein the pan motor assembly is attached to the linkage assembly such that the pan motor assembly extends with the linkage assembly when the linkage assembly extends along the first axis.

16. The adjustable image capture device of claim 13, wherein the housing comprises a cavity, wherein the pan motor assembly is sized and configured to fit within the cavity.

17. The adjustable image capture device of claim 16, wherein the pan motor assembly is positioned within the cavity when the linkage assembly is in the first state.

18. An adjustable image capture device comprising:
a housing;
a linkage assembly, the linkage assembly having a bore, the linkage assembly comprising a plurality of linkages, wherein each linkage of the plurality of linkages has a gear rack, and wherein each linkage having a bore, wherein the bores of the plurality of linkages defining the bore of the linkage assembly; and
an extension motor assembly, wherein the extension motor assembly comprises:
a gear, and
a motor, and
wherein the gear has teeth that mesh with teeth of the gear rack, wherein the motor is configured to impart motion to the gear, and wherein the extension motor assembly is configured to extend the linkage assembly along a longitudinal axis; and
an image capture device, wherein the image capture device is configured to fit within the bore of the linkage assembly;
wherein the linkage assembly is configured to fit within the housing;
wherein, when the linkage assembly is in a first state, each linkage of the plurality of linkages are positioned inside a channel of the housing;
wherein, when the linkage assembly is in a second state, one or more of the linkages of the plurality of linkages are positioned outside the channel of the housing;
wherein extension motor assembly is configured to transition the linkage assembly from the first state to the second state.

19. The adjustable image capture device of claim 18, the second state comprising a plurality of sub-states, wherein each sub-state of the plurality of sub-states defines a position of a linkage relative to the housing; and
wherein each sub-state of the plurality of sub-states is associated with a position of the teeth of the gear relative to the teeth of the gear rack.

20. The adjustable image capture device of claim 18, further comprising:
a tilt motor assembly, wherein the tilt motor assembly comprises:
a motor; and
wherein the motor is attached to the image capture device, and wherein the motor is configured to impart motion to the image capture device.

21. The adjustable image capture device of claim 20, wherein the image capture device comprises a borescope camera, wherein the borescope camera has a field of view, and wherein the borescope camera is configured such that the field of view is biased in a first direction.

22. The adjustable image capture device of claim 21, wherein, when the tilt motor assembly is activated, the field of view is adjusted to a second direction and wherein there is angle between the first direction and the second direction.

23. The adjustable image capture device of claim 18, further comprising:
a pan motor assembly, wherein the pan motor assembly comprises:
a motor; and
wherein the motor is attached to the image capture device, and wherein the motor is configured to impart motion to the image capture device.

24. The adjustable image capture device of claim 18, wherein the motor comprises a servo-motor.

25. An adjustable image capture device comprising:
a housing;
a linkage assembly, the linkage assembly having a bore, the linkage assembly comprising a plurality of linkages, wherein each linkage of the plurality of linkages has a gear rack, and wherein each linkage having a bore, wherein the bores of the plurality of linkages defining the bore of the linkage assembly; and
an extension motor assembly, wherein the extension motor assembly comprises:
a gear, and
a first motor, and
wherein the gear has teeth that mesh with teeth of the gear rack, and wherein the first motor is configured to impart motion to the gear, and wherein the extension motor assembly is configured to extend the linkage assembly along a first axis;
a borescope camera, wherein the borescope camera is configured to fit within a bore of the linkage assembly;
a pan motor assembly, wherein the pan motor assembly comprises a second motor, wherein the second motor is coupled to the borescope camera, wherein pan motor assembly is configured to rotate a field of view of the borescope camera about a second axis; and
an tilt motor assembly, wherein the tilt motor assembly comprises a third motor, wherein the third motor is attached to the borescope camera, and wherein the tilt motor assembly is configured to rotate the field of view of the borescope camera about a third axis, wherein the second axis is perpendicular to the third axis;
wherein the linkage assembly is configured to fit within the housing;
wherein, when the linkage assembly is in a first state, each linkage of the plurality of linkages are positioned inside a channel of the housing;
wherein, when the linkage assembly is in a second state, one or more of the linkages of the plurality of linkages are positioned outside the channel of the housing;
wherein extension motor assembly is configured to transition the linkage assembly from the first state to the second state.

26. The adjustable image capture device of claim 25, wherein the borescope camera has a field of view and wherein the borescope camera is configured such that the field of view is biased such that the field of view is in a first direction.

27. The adjustable image capture device of claim 26, wherein, when the tilt motor assembly is activated, the field of view is adjusted to a second direction and wherein there is angle between the first direction and the second direction.

28. The adjustable image capture device of claim 25, wherein the bore of a linkage is a primary bore, wherein the plurality of linkages comprises a first linkage and a second linkage;
wherein the first linkage has one or more secondary bores and the second linkage has one or more secondary bores;
wherein the one or more secondary bores of the first linkage are adjacent the primary bore of the first linkage, wherein the one or more secondary bores of the second linkage are adjacent the primary bore of the second linkage;
wherein a line is positioned in the one or more secondary bores of the first linkage and is positioned in the one or more secondary bores of the second linkage, wherein the line couples the first linkage to the second linkage.

29. The adjustable image capture device of claim 25, wherein at least one of the first motor, the second motor, or the third motor comprises a servo-motor.

30. The adjustable image capture device of claim 25, wherein the housing has an opening that provides access the channel, and wherein the linkages of the linkage assembly are configured to fit through the opening.

\* \* \* \* \*